US010632307B2

(12) United States Patent
Parker

(10) Patent No.: US 10,632,307 B2
(45) Date of Patent: Apr. 28, 2020

(54) NEURAL STIMULATION DOSING

(71) Applicant: Saluda Medical Pty Ltd, Artarmon (AU)

(72) Inventor: John Louis Parker, Artarmon (AU)

(73) Assignee: Saluda Medical Pty Ltd, Artarmon (AU)

( * ) Notice: Subject to any disclaimer, the term of this patent is extended or adjusted under 35 U.S.C. 154(b) by 542 days.

(21) Appl. No.: 15/327,981

(22) PCT Filed: Jul. 27, 2015

(86) PCT No.: PCT/US2015/050422
§ 371 (c)(1),
(2) Date: Jan. 20, 2017

(87) PCT Pub. No.: WO2016/011512
PCT Pub. Date: Jan. 28, 2016

(65) Prior Publication Data
US 2017/0216587 A1    Aug. 3, 2017

(30) Foreign Application Priority Data

Jul. 25, 2014  (AU) ............................... 2014902897
Mar. 13, 2015  (AU) ............................... 2015900912

(51) Int. Cl.
*A61N 1/36*    (2006.01)
*A61N 1/05*    (2006.01)
(Continued)

(52) U.S. Cl.
CPC ............ *A61N 1/3605* (2013.01); *A61N 1/05* (2013.01); *A61N 1/0551* (2013.01); *A61N 1/06* (2013.01); *A61N 1/36* (2013.01); *A61N 1/36071* (2013.01); *A61N 1/36146* (2013.01); *A61N 1/36171* (2013.01); *A61N 1/36175* (2013.01); *A61N 1/36178* (2013.01); *A61N 1/36185* (2013.01);
(Continued)

(58) Field of Classification Search
CPC ....... A61N 1/0551; A61N 1/3605; A61N 1/05
USPC .......................................................... 607/46
See application file for complete search history.

(56) References Cited

U.S. PATENT DOCUMENTS 3,736,434 A    5/1973  Darrow
3,817,254 A    6/1974  Maurer
(Continued)

FOREIGN PATENT DOCUMENTS

EP    0219084       4/1987
EP    0998958 B1    8/2005
(Continued)

OTHER PUBLICATIONS

European Search Report for European Application No. 15861444.6, Search completed Jul. 13, 2018, dated Jul. 23, 2018, 8 pgs.
(Continued)

*Primary Examiner* — Nadia A Mahmood
(74) *Attorney, Agent, or Firm* — KPPB LLP

(57) ABSTRACT

Applying therapeutic neural stimuli involves monitoring for at least one of sensory input and movement of a user. In response to detection of sensory input or user movement, an increased stimulus dosage is delivered within a period of time corresponding to a duration of time for which the detected sensory input or user movement gives rise to masking, the increased stimulus dosage being configured to give rise to increased neural recruitment.

26 Claims, 11 Drawing Sheets

(51) Int. Cl.
*A61N 1/06* (2006.01)
*A61N 1/372* (2006.01)

(52) U.S. Cl.
CPC ...... *A61N 1/37247* (2013.01); *A61N 1/36021* (2013.01)

(56) References Cited

U.S. PATENT DOCUMENTS

| | | |
|---|---|---|
| 3,898,472 A | 8/1975 | Long |
| 4,158,196 A | 6/1979 | Crawford, Jr. |
| 4,418,695 A | 12/1983 | Buffet |
| 4,474,186 A | 10/1984 | Ledley et al. |
| 4,628,934 A | 12/1986 | Pohndorf et al. |
| 4,807,643 A | 2/1989 | Rosier |
| 4,856,525 A | 8/1989 | Van Den et al. |
| 5,113,859 A | 5/1992 | Funke |
| 5,139,020 A | 8/1992 | Koestner et al. |
| 5,143,081 A | 9/1992 | Young et al. |
| 5,156,154 A | 10/1992 | Valenta, Jr. et al. |
| 5,172,690 A | 12/1992 | Nappholz et al. |
| 5,184,615 A | 2/1993 | Nappholz et al. |
| 5,188,106 A | 2/1993 | Nappholz et al. |
| 5,215,100 A | 6/1993 | Spitz |
| 5,324,311 A | 6/1994 | Acken |
| 5,417,719 A | 5/1995 | Hull et al. |
| 5,431,693 A | 7/1995 | Schroeppel |
| 5,458,623 A | 10/1995 | Lu et al. |
| 5,476,486 A | 12/1995 | Lu et al. |
| 5,497,781 A | 3/1996 | Chen et al. |
| 5,638,825 A | 6/1997 | Yamazaki et al. |
| 5,702,429 A | 12/1997 | King et al. |
| 5,758,651 A | 6/1998 | Nygard et al. |
| 5,776,170 A | 7/1998 | Macdonald et al. |
| 5,785,651 A | 7/1998 | Kuhn et al. |
| 5,792,212 A | 8/1998 | Weijand et al. |
| 5,814,092 A | 9/1998 | King |
| 5,913,882 A | 6/1999 | King |
| 5,999,848 A | 12/1999 | Gord et al. |
| 6,020,857 A | 2/2000 | Podger |
| 6,027,456 A | 2/2000 | Feler et al. |
| 6,038,480 A | 3/2000 | Hrdlicka et al. |
| 6,066,163 A | 5/2000 | John |
| 6,114,164 A | 9/2000 | Dennis et al. |
| 6,144,881 A | 11/2000 | Hemming et al. |
| 6,157,861 A | 12/2000 | Faltys et al. |
| 6,212,431 B1 | 4/2001 | Hahn et al. |
| 6,246,912 B1 | 6/2001 | Sluijter et al. |
| 6,381,496 B1 | 4/2002 | Meadows et al. |
| 6,449,512 B1 | 9/2002 | Boveja |
| 6,463,328 B1 | 10/2002 | John |
| 6,473,649 B1 | 10/2002 | Gryzwa et al. |
| 6,473,653 B1 | 10/2002 | Schallhorn et al. |
| 6,493,576 B1 | 12/2002 | Dankwart-Eder |
| 6,522,932 B1 | 2/2003 | Kuzma |
| 6,600,955 B1 | 7/2003 | Zierhofer et al. |
| 6,658,293 B2 | 12/2003 | Vonk et al. |
| 6,675,046 B2 | 1/2004 | Holsheimer |
| 6,782,292 B2 | 8/2004 | Whitehurst |
| 6,898,582 B2 | 5/2005 | Lange et al. |
| 7,089,059 B1 | 8/2006 | Pless |
| 7,171,261 B1 | 1/2007 | Litvak et al. |
| 7,231,254 B2 | 6/2007 | DiLorenzo et al. |
| 7,286,876 B2 | 10/2007 | Yonce et al. |
| 7,412,287 B2 | 8/2008 | Yonce et al. |
| 7,450,992 B1 | 11/2008 | Cameron |
| 7,734,340 B2 | 6/2010 | De Ridder |
| 7,742,810 B2 | 6/2010 | Moffitt |
| 7,792,584 B2 | 9/2010 | Van Oort et al. |
| 7,818,052 B2 | 10/2010 | Litvak et al. |
| 7,831,305 B2 | 11/2010 | Gliner |
| 7,835,804 B2 | 11/2010 | Fridman et al. |
| 8,190,251 B2 | 5/2012 | Molnar et al. |
| 8,224,459 B1 | 7/2012 | Pianca et al. |
| 8,239,031 B2 | 8/2012 | Fried et al. |
| 8,359,102 B2 | 1/2013 | Thacker et al. |
| 8,417,342 B1 | 4/2013 | Abell |
| 8,454,529 B2 | 6/2013 | Daly et al. |
| 8,494,645 B2 | 7/2013 | Spitzer et al. |
| 8,588,929 B2 | 11/2013 | Davis et al. |
| 8,670,830 B2 | 3/2014 | Carlson et al. |
| 8,886,323 B2 | 11/2014 | Wu et al. |
| 9,155,892 B2 | 10/2015 | Parker et al. |
| 9,302,112 B2 | 4/2016 | Bornzin et al. |
| 9,381,356 B2 | 7/2016 | Parker et al. |
| 9,386,934 B2 | 7/2016 | Parker et al. |
| 9,872,990 B2 | 1/2018 | Parker et al. |
| 9,974,455 B2 | 5/2018 | Parker et al. |
| 10,206,596 B2 | 2/2019 | Single et al. |
| 10,278,600 B2 | 5/2019 | Parker et al. |
| 10,368,762 B2 | 8/2019 | Single |
| 2002/0055688 A1 | 5/2002 | Katims |
| 2002/0099419 A1 | 7/2002 | Ayal et al. |
| 2002/0193670 A1 | 12/2002 | Garfield et al. |
| 2003/0032889 A1 | 2/2003 | Wells |
| 2003/0045909 A1 | 3/2003 | Gross et al. |
| 2003/0139781 A1 | 7/2003 | Bradley et al. |
| 2003/0195580 A1 | 10/2003 | Bradley et al. |
| 2004/0088017 A1 | 5/2004 | Sharma et al. |
| 2004/0122482 A1 | 6/2004 | Tung et al. |
| 2004/0158298 A1 | 8/2004 | Gliner |
| 2004/0225211 A1 | 11/2004 | Gozani et al. |
| 2004/0254494 A1 | 12/2004 | Spokoyny et al. |
| 2005/0010265 A1 | 1/2005 | Baru Fassio |
| 2005/0017190 A1 | 1/2005 | Eversmann et al. |
| 2005/0021104 A1 | 1/2005 | DiLorenzo |
| 2005/0065427 A1 | 3/2005 | Magill |
| 2005/0070982 A1 | 3/2005 | Heruth et al. |
| 2005/0075683 A1 | 4/2005 | Miesel et al. |
| 2005/0101878 A1 | 5/2005 | Daly |
| 2005/0113877 A1 | 5/2005 | Giardiello et al. |
| 2005/0137670 A1 | 6/2005 | Christopherson et al. |
| 2005/0149154 A1 | 7/2005 | Cohen |
| 2005/0192567 A1 | 9/2005 | Katims |
| 2005/0203600 A1 | 9/2005 | Wallace |
| 2005/0209655 A1 | 9/2005 | Bradley et al. |
| 2005/0282149 A1 | 12/2005 | Kovacs et al. |
| 2006/0009820 A1 | 1/2006 | Royle et al. |
| 2006/0020291 A1 | 1/2006 | Gozani |
| 2006/0135998 A1 | 6/2006 | Libbus et al. |
| 2006/0195159 A1 | 8/2006 | Bradley et al. |
| 2006/0212089 A1 | 9/2006 | Tass |
| 2006/0217782 A1 | 9/2006 | Boveja et al. |
| 2006/0264752 A1 | 11/2006 | Rubinsky et al. |
| 2006/0287609 A1 | 12/2006 | Litvak et al. |
| 2007/0021800 A1 | 1/2007 | Bradley et al. |
| 2007/0073354 A1 | 3/2007 | Knudson et al. |
| 2007/0100378 A1 | 5/2007 | Maschino |
| 2007/0178579 A1 | 8/2007 | Ross et al. |
| 2007/0185409 A1 | 8/2007 | Wu et al. |
| 2007/0208394 A1 | 9/2007 | King et al. |
| 2007/0225767 A1 | 9/2007 | Daly et al. |
| 2007/0244410 A1 | 10/2007 | Fridman et al. |
| 2007/0250120 A1 | 10/2007 | Flach et al. |
| 2007/0255372 A1 | 11/2007 | Metzler et al. |
| 2007/0282217 A1 | 12/2007 | McGinnis et al. |
| 2007/0287931 A1 | 12/2007 | Dilorenzo |
| 2008/0021292 A1 | 1/2008 | Stypulkowski |
| 2008/0051647 A1 | 2/2008 | Wu et al. |
| 2008/0064947 A1 | 3/2008 | Heruth et al. |
| 2008/0077191 A1 | 3/2008 | Morrell |
| 2008/0097529 A1 | 4/2008 | Parramon et al. |
| 2008/0147155 A1 | 6/2008 | Swoyer |
| 2008/0183076 A1 | 7/2008 | Witte |
| 2008/0208304 A1 | 8/2008 | Zdravkovic et al. |
| 2008/0234780 A1 | 9/2008 | Smith et al. |
| 2008/0275527 A1 | 11/2008 | Greenberg et al. |
| 2008/0294221 A1 | 11/2008 | Kilgore |
| 2008/0300655 A1 | 12/2008 | Cholette |
| 2008/0319508 A1 | 12/2008 | Botros et al. |
| 2009/0033486 A1 | 2/2009 | Costantino et al. |
| 2009/0082691 A1 | 3/2009 | Denison et al. |
| 2009/0149912 A1 | 6/2009 | Dacey, Jr. et al. |
| 2009/0157155 A1 | 6/2009 | Bradley |
| 2009/0270957 A1 | 10/2009 | Pianca |

(56) References Cited

U.S. PATENT DOCUMENTS

| | | |
|---|---|---|
| 2009/0287277 A1 | 11/2009 | Conn et al. |
| 2009/0299214 A1 | 12/2009 | Wu et al. |
| 2009/0306491 A1 | 12/2009 | Haggers |
| 2010/0010388 A1 | 1/2010 | Panken et al. |
| 2010/0058126 A1 | 3/2010 | Chang et al. |
| 2010/0069835 A1 | 3/2010 | Parker |
| 2010/0069996 A1 | 3/2010 | Strahl |
| 2010/0070007 A1 | 3/2010 | Parker |
| 2010/0070008 A1 | 3/2010 | Parker |
| 2010/0106231 A1 | 4/2010 | Torgerson |
| 2010/0114237 A1 | 5/2010 | Giftakis et al. |
| 2010/0114258 A1 | 5/2010 | Donofrio et al. |
| 2010/0125313 A1 | 5/2010 | Lee et al. |
| 2010/0125314 A1 | 5/2010 | Bradley et al. |
| 2010/0145222 A1 | 6/2010 | Brunnett et al. |
| 2010/0152808 A1 | 6/2010 | Boggs |
| 2010/0179626 A1 | 7/2010 | Pilarski |
| 2010/0191307 A1 | 7/2010 | Fang et al. |
| 2010/0204748 A1 | 8/2010 | Lozano et al. |
| 2010/0222844 A1 | 9/2010 | Troosters et al. |
| 2010/0222858 A1 | 9/2010 | Meloy |
| 2010/0249643 A1 | 9/2010 | Gozani et al. |
| 2010/0249867 A1 | 9/2010 | Wanasek |
| 2010/0258342 A1 | 10/2010 | Parker |
| 2010/0262208 A1 | 10/2010 | Parker |
| 2010/0262214 A1 | 10/2010 | Robinson |
| 2010/0280570 A1 | 11/2010 | Sturm et al. |
| 2010/0286748 A1 | 11/2010 | Midani et al. |
| 2010/0331604 A1 | 12/2010 | Okamoto et al. |
| 2010/0331926 A1 | 12/2010 | Lee et al. |
| 2011/0004207 A1 | 1/2011 | Wallace et al. |
| 2011/0021943 A1 | 1/2011 | Lacour et al. |
| 2011/0028859 A1 | 2/2011 | Chian |
| 2011/0087085 A1 | 4/2011 | Tsampazis et al. |
| 2011/0093042 A1 | 4/2011 | Torgerson et al. |
| 2011/0106100 A1 | 5/2011 | Bischoff |
| 2011/0184488 A1 | 7/2011 | De Ridder et al. |
| 2011/0204811 A1 | 8/2011 | Pollmann-retsch |
| 2011/0224665 A1 | 9/2011 | Crosby et al. |
| 2011/0224749 A1 | 9/2011 | Ben-David et al. |
| 2011/0264165 A1 | 10/2011 | Molnar et al. |
| 2011/0270343 A1 | 11/2011 | Buschman et al. |
| 2011/0307030 A1 | 12/2011 | John |
| 2011/0313310 A1 | 12/2011 | Tomita |
| 2011/0313483 A1 | 12/2011 | Hincapie et al. |
| 2012/0029377 A1 | 2/2012 | Polak |
| 2012/0101552 A1 | 4/2012 | Lazarewicz et al. |
| 2012/0109236 A1 | 5/2012 | Jacobson et al. |
| 2012/0253423 A1 | 10/2012 | Youn et al. |
| 2012/0277621 A1 | 11/2012 | Gerber et al. |
| 2012/0277823 A1 | 11/2012 | Gerber et al. |
| 2013/0053722 A1 | 2/2013 | Carlson et al. |
| 2013/0060302 A1 | 3/2013 | Polefko et al. |
| 2013/0172774 A1 | 7/2013 | Crowder et al. |
| 2013/0289661 A1 | 10/2013 | Griffith et al. |
| 2013/0289683 A1 | 10/2013 | Parker et al. |
| 2014/0066803 A1 | 3/2014 | Choi |
| 2014/0142447 A1 | 5/2014 | Takahashi et al. |
| 2014/0194771 A1 | 7/2014 | Parker et al. |
| 2014/0194772 A1 | 7/2014 | Single et al. |
| 2014/0236042 A1 | 8/2014 | Parker et al. |
| 2014/0236257 A1 | 8/2014 | Parker et al. |
| 2014/0243926 A1 | 8/2014 | Carcieri |
| 2014/0243931 A1 | 8/2014 | Parker et al. |
| 2014/0276195 A1 | 9/2014 | Papay et al. |
| 2014/0277250 A1 | 9/2014 | Su et al. |
| 2014/0288551 A1 | 9/2014 | Bharmi et al. |
| 2014/0288577 A1 | 9/2014 | Robinson et al. |
| 2014/0296737 A1 | 10/2014 | Parker et al. |
| 2014/0358024 A1 | 12/2014 | Nelson et al. |
| 2015/0018699 A1 | 1/2015 | Zeng et al. |
| 2015/0164354 A1 | 6/2015 | Parker et al. |
| 2015/0174396 A1 | 6/2015 | Fisher et al. |
| 2015/0238104 A1 | 8/2015 | Tass |
| 2015/0238304 A1 | 8/2015 | Lamraoui |
| 2015/0282725 A1 | 10/2015 | Single |
| 2015/0313487 A1 | 11/2015 | Single |
| 2015/0360031 A1 | 12/2015 | Bornzin et al. |
| 2015/0374999 A1 | 12/2015 | Parker |
| 2016/0129272 A1 | 5/2016 | Hou et al. |
| 2016/0166164 A1 | 6/2016 | Obradovic et al. |
| 2016/0175594 A1 | 6/2016 | Min et al. |
| 2016/0287126 A1 | 10/2016 | Parker et al. |
| 2016/0287182 A1 | 10/2016 | Single |
| 2017/0001017 A9 | 1/2017 | Parker et al. |
| 2017/0049345 A1 | 2/2017 | Single |
| 2017/0071490 A1 | 3/2017 | Parker et al. |
| 2017/0135624 A1 | 5/2017 | Parker |
| 2017/0361101 A1 | 12/2017 | Single |
| 2018/0110987 A1 | 4/2018 | Parker |
| 2018/0117335 A1 | 5/2018 | Parker et al. |
| 2018/0132747 A1 | 5/2018 | Parker et al. |
| 2018/0132760 A1 | 5/2018 | Parker |
| 2018/0133459 A1 | 5/2018 | Parker et al. |
| 2018/0228391 A1 | 8/2018 | Parker et al. |
| 2018/0228547 A1 | 8/2018 | Parker |
| 2018/0229046 A1 | 8/2018 | Parker et al. |
| 2018/0256052 A1 | 9/2018 | Parker et al. |
| 2019/0168000 A1 | 6/2019 | Laird-wah |
| 2019/0216343 A1 | 7/2019 | Single et al. |
| 2019/0239768 A1 | 8/2019 | Karantonis et al. |

FOREIGN PATENT DOCUMENTS

| | | |
|---|---|---|
| EP | 2019716 A | 11/2007 |
| EP | 2243510 A2 | 10/2010 |
| EP | 2443995 A2 | 4/2012 |
| EP | 2707095 A1 | 3/2014 |
| JP | 2012524629 | 10/2012 |
| JP | 2013527784 A | 7/2013 |
| JP | 2013536044 A | 9/2013 |
| WO | 1983003191 A | 9/1983 |
| WO | 1993001863 A1 | 2/1993 |
| WO | 9612383 A1 | 4/1996 |
| WO | 2000002623 A1 | 1/2000 |
| WO | 2002036003 A1 | 11/2001 |
| WO | 2002038031 | 5/2002 |
| WO | 2002049500 A2 | 6/2002 |
| WO | 2003028521 A2 | 4/2003 |
| WO | 2003043690 | 5/2003 |
| WO | 2003103484 | 12/2003 |
| WO | 2004021885 A1 | 3/2004 |
| WO | 20040103455 | 12/2004 |
| WO | 2005032656 A1 | 4/2005 |
| WO | 2005105202 A1 | 11/2005 |
| WO | 2006091636 A2 | 8/2006 |
| WO | 2007064936 A1 | 6/2007 |
| WO | 2007127926 A2 | 11/2007 |
| WO | 2007130170 A1 | 11/2007 |
| WO | 2008004204 A1 | 1/2008 |
| WO | 2008049199 A1 | 5/2008 |
| WO | 2009002072 A2 | 12/2008 |
| WO | 2009002579 A1 | 12/2008 |
| WO | 2009010870 A2 | 1/2009 |
| WO | 2009130515 A2 | 10/2009 |
| WO | 2009146427 A1 | 12/2009 |
| WO | 2010013170 A1 | 2/2010 |
| WO | 2010044989 A2 | 4/2010 |
| WO | 2010051392 A1 | 5/2010 |
| WO | 2010057046 A2 | 5/2010 |
| WO | 2010124139 A1 | 10/2010 |
| WO | 2010138915 A1 | 12/2010 |
| WO | 2011011327 A1 | 1/2011 |
| WO | 2011066477 A1 | 6/2011 |
| WO | 2011066478 A1 | 6/2011 |
| WO | 2011112843 A1 | 9/2011 |
| WO | 2011119251 A2 | 9/2011 |
| WO | 2011159545 A2 | 12/2011 |
| WO | 2012027252 A2 | 3/2012 |
| WO | 2012027791 A1 | 3/2012 |
| WO | 2012155183 A1 | 11/2012 |
| WO | 2012155184 A1 | 11/2012 |
| WO | 2012155185 A1 | 11/2012 |
| WO | 2012155187 A1 | 11/2012 |

(56) References Cited

FOREIGN PATENT DOCUMENTS

| | | | |
|---|---|---|---|
| WO | 2012155188 A1 | 11/2012 |
| WO | 2012155189 A1 | 11/2012 |
| WO | 2012155190 A1 | 11/2012 |
| WO | 2013063111 A1 | 5/2013 |
| WO | 2013075171 A1 | 5/2013 |
| WO | 2014071445 A1 | 5/2014 |
| WO | 2014071446 A1 | 5/2014 |
| WO | 2014143577 A1 | 9/2014 |
| WO | 2015070281 A1 | 5/2015 |
| WO | 2015074121 A1 | 5/2015 |
| WO | 2015109239 A1 | 7/2015 |
| WO | 2015143509 A1 | 10/2015 |
| WO | 2015168735 A1 | 11/2015 |
| WO | 20160011512 | 1/2016 |
| WO | 2016077882 A1 | 5/2016 |
| WO | 2016090420 A1 | 6/2016 |
| WO | 2016090436 A1 | 6/2016 |
| WO | 2016115596 A1 | 7/2016 |
| WO | 2016161484 A2 | 10/2016 |
| WO | 2016191807 A1 | 12/2016 |
| WO | 2016191808 A1 | 12/2016 |
| WO | 2016191815 A1 | 12/2016 |
| WO | 2017173493 A1 | 10/2017 |
| WO | 2017219096 A1 | 12/2017 |

OTHER PUBLICATIONS

International Search Report and Written Opinion for International Application No. PCT/AU2017/050296, Search Completed Jul. 28, 2017, dated Jul. 28, 2017, 10 pgs.

Partial European Search Report for European Application No. 16775966.1, Search completed Oct. 26, 2018, dated Nov. 6, 2018, 11 Pgs.

He et al., "Perception threshold and electrode position for spinal cord stimulation", Pain, 59 (1994) 55-63 pages.

Holsheimer et al., "Significance of the Spinal Cord Position in Spinal Cord Stimulation", Acta Neurochir (1995) [Suppl] 64: 119-124 pages.

Holsheimer et al., "Spinal Geometry and Paresthesia Coverage in Spinal Cord Stimulation", (1998 paper) 8 pages.

Olin et al., "Postural Changes in Spinal Cord Stimulation Perceptual Thresholds", Neuromodulation, vol. 1, No. 4, 1998, pp. 171-175.

Rattay, "Analysis of Models for External Stimulation of Axons", IEEE Transactions on Biomedical Engineering, vol. BME-33, No. 10, Oct. 1986, pp. 974-977.

Ross et al., "Improving Patient Experience with Spinal Cord Stimulation: Implications of Position-Related Changes in Neurostimulation", Neuromodulation 2011; e-pub ahead of print. DOI: 10.1111/j.1525-1403.2011.00407.x 6 pages.

Struijk, "The Extracellular Potential of a Myelinated Nerve Fiber in an Unbounded Medium and in Nerve Cuff Models", Biophysical Journal vol. 72 Jun. 1997 2457-2469.

Extended European Search Report for European Application No. 15768956.3, Search completed Oct. 3, 2017, dated Oct. 10, 2017, 8 Pgs.

Parker et al., "Closing the Loop in Neuromodulation Therapies: Spinal Cord Evoked Compound Action Potentials During Stimulation for Pain Management (230).", 2011, In 15th Annual Meeting, North American Neuromodulation Society (p. 48). Presented at the North American Neuromodulation Society, Las Vegas.

Parker et al., "Compound action potentials recorded in the human spinal cord during neurostimulation for pain relief", Pain, 2012, vol. 153, pp. 593-601.

Parker et al., "Electrically Evoked Compound Action Potentials Recorded From the Sheep Spinal Cord", Neuromodulation, vol. 16, 2013, pp. 295-303.

Penar et al., "Cortical Evoked Potentials Used for Placement of a Laminotomy Lead Array: A Case Report", Neuromodulation: Technology at the Neural Interface, accessed Apr. 19, 2011, doi:10.1111/j.1525-1403.2011.00352.x.

Richter et al., "EMG and SSEP Monitoring During Cervical Spinal Cord Stimulation", Journal of Neurosurgical Review 2011, Southern Academic Press, 1(S1), 2001, pp. 61-63.

Ridder et al., "Burst Spinal Cord Stimulation for Limb and Back Pain", World Neurosurgery, 2013, 9 pgs.

Ridder et al., "Burst Spinal Cord Stimulation toward Paresthesia-Free Pain Suppression", May 2010, vol. 66, pp. 986-990.

Roy, S. H. et al., "Effects of Electrode Location on Myoelectric Conduction Velocity and Median Frequency Estimates", J. Appl. Physiol. 61 (4), 1986, pp. 1510-1517.

Schmidt et al., "Gating of tactile input from the hand", Exp Brain Res, 1990, 79, pp. 97-102.

Siegfried et al., "Bilateral Chronic Electrostimulation of Ventroposterolateral Pallidum: A New Therapeutic Approach for Alleviating all Parkinsonian Symptoms", Neurosurgery, 35, No. 6, Dec. 1994, pp. 1126-1130.

Siegfried et al., "Intracerebral Electrode Implantation System", Journal of Neurosurgery, vol. 59, No. 2, Aug. 1983, pp. 356-3591.

Srinivasan, S, "Electrode/Electrolyte Interfaces: Structure and Kinetics of Charge Transfer", Fuel Cells, 2006, Chapter 2, 67 pgs.

Struijk et al, "Paresthesia Thresholds in Spinal Cord Stimulation: A Comparison of Theoretical Results with Clinical Data", IEEE Transactions on Rehabilitation Engineering, vol. 1, No. 2, Jun. 1993, pp. 101-108.

Sufka et al., "Gate Control Theory Reconsidered", Brain and Mind, 3, No. 2, 2002, pp. 277-290.

Tamura et al., "Increased Nodal Persistent Na+ Currents in Human Neuropathy and Motor Neuron Disease Estimated by Latent Addition", Clinical Neurophysiology 117, No. 11 (Nov. 2006): 2451-2458, doi:10.1016/j.clinph.2006.07.309.

Tasker, "Deep Brain Stimulation is Preferable to Thalamotomy for Tremor Suppression", Surgical Neurology, 49, No. 2, 1998, pp. 145-153.

Taylor et al., "Spinal Cord Stimulation for Chronic Back and Leg Pain and Failed Back Surgery Syndrome: A Systematic Review and Analysis of Prognostic Factors", Spine, vol. 30, No. 1, pp. 152-160.

Texas Instruments, "Precision, Low Power Instrumentation Amplifiers", Texas Instruments SBOS051B Oct. 1995, Revised Feb. 2005, 20 pgs.

Tomas et al., "Dorsal Root Entry Zone (DREZ) Localization Using Direct Spinal Cord Stimulation Can Improve Results of the DREZ Thermocoagulation Procedure for Intractable Pain Relief", Pain, 2005, vol. 116, pp. 159-163.

Tscherter et al., "Spatiotemporal Characterization of Rhythmic Activity in Rat Spinal Cord Slice Cultures", European Journal of Neuroscience 14, No. 2 (2001), pp. 179-190.

Van Den Berg et al., "Nerve fiber size-related block of action currents by phenytoin in mammalian nerve", Epilepsia, Nov. 1994, 35(6), pp. 1279-1288.

Villavicencio, Alan T., "Laminectomy versus Percutaneous Electrode Placement for Spinal Cord Stimulation," Neurosurgery, vol. 46 (2), Feb. 2000, pp. 399-405.

Vleggeert et al., LANKAMP, "Electrophysiology and morphometry of the Aalpha- and Abeta-fiber populations in the normal and regenerating rat sciatic nerve", Experimental Neurology, vol. 187, No. 2, Jun. 1, 2004, Available online Apr. 2, 2004, pp. 337-349.

Woessner, "Blocking Out the Pain, Electric Nerve Block Treatments for Sciatic Neuritis", Retrieved from: http://www.practicalpainmanagement.com/pain/spine/radiculopathy/blocking-out-pain, Last updated Jan. 10, 2012.

Wolter et al., "Effects of sub-perception threshold spinal cord stimulation in neuropathic pain: A randomized controlled double-blind crossover study", European Federation of International Association for the Study of Pain Chapters, 2012, pp. 648-655.

Wu et al., "Changes in Aβ Non-nociceptive Primary Sensory Neurons in a Rat Model of Osteoarthritis Pain", Molecular Pain 6, No. 1 (Jul. 1, 2010): 37, doi: 10.1186/1744-8069-6-37.

Xie et al., "Functional Changes in Dorsal Root Ganglion Cells after Chronic Nerve Constriction in the Rat", Journal of Neurophysiology 73, No. 5 (May 1, 1995): 1811-1820.

Xie et al., "Sinusoidal Time-Frequency Wavelet Family and its Application in Electrograstrographic Signal Analysis", Proceedings

(56) References Cited

OTHER PUBLICATIONS of the 20th Annual International Conference of the IEEE Engineering in Medicine and Biology Society, vol. 20, No. 3, Oct. 29, 1998, pp. 1450-1453.
Yearwood, T. L., "Pulse Width Programming in Spinal Cord Stimulation: a Clinical Study", Pain Physician. 2010. vol. 13, pp. 321-335.
Yingling et al., "Use of Antidromic Evoked Potentials in Placement of Dorsal Cord Disc Electrodes", Applied Neurophysiology, 1986, vol. 49, pp. 36-41. Whole Document.
Yuan, S. et al., "Recording monophasic action potentials using a platinum-electrode ablation catheter", Europace Oct. 2000; 2(4):312-9; Abstract.
International Preliminary Report on Patentability for International Application No. PCT/AU2015/050753, Report dated Jun. 13, 2017, 7 pgs.
International Search Report and Written Opinion for International Application No. PCT/AU2016/050263, Search completed Nov. 16, 2016, dated Nov 16, 2016, 8 Pgs.
International Search Report and Written Opinion for International Application No. PCT/AU2016/050430, Search completed Aug. 16, 2016, dated Aug. 16, 2016, 10 Pgs.
International Search Report and Written Opinion for International Application No. PCT/AU2016/050431, Search completed Aug. 16, 2016, dated Aug. 16, 2016, 11 Pgs.
International Search Report and Written Opinion for International Application No. PCT/AU2016/050439, Search completed Jul. 15, 2016, dated Jul. 15, 2016, 8 Pgs.
Alam et al., "Evaluation of optimal electrode configurations for epidural spinal cord stimulation in cervical spinal cord injured rats", Journal of Neuroscience Methods, Mar. 2015, 28 pgs.
Fisher, "F-Waves—Physiology and Clinical Uses", The Scientific World Journal, (2007) 7, pp. 144-160.
Gad et al., "Development of a multi-electrode array for spinal cord epidural stimulation to facilitate stepping and standing after a complete spinal cord injury in adult rats", Journal of NeuroEngineering and Rehabilitation 2013, 10:2, 18 pgs.
Sayenko et al., "Neuromodulation of evoked muscle potentials induced by epidural spinal-cord stimulation in paralyzed individuals", Journal of Neurophysiology, vol. 111, No. 5, 2014, pp. 1088-1099, First published Dec. 11, 2013.
Struijk et al., "Excitation of Dorsal Root Fibers in Spinal Cord Stimulation: a Theoretical Study", IEEE Transactions on Biomedical Engineering, Jul. 1993, vol. 40, No. 7, pp. 632-639.
Yamada et al., "Extraction and Analysis of the Single Motor Unit F-Wave of the Median Nerve", EMG Methods for Evaluating Muscle and Nerve Function, InTech, 2012, 15 pgs.
Al-Ani et al., "Automatic removal of high-amplitude stimulus artefact from neuronal signal recorded in the subthalamic nucleus", Journal of Neuroscience Methods, vol. 198, Issue 1, 2011, pp. 135-146.
European Search Report for European Application 12785619.3 Search Completed Oct. 13, 2014, dated Oct. 23, 2014, 7 pgs.
European Search Report for European Application 12785669.8 Search Completed Sep. 22, 2014, dated Sep. 29, 2014, 5 pgs.
Extended European Search Report for EP Application 12785483.4 completed Sep. 16, 2014, 7 pgs.
Extended European Search Report for European Application No. 11820923.8, report completed Dec. 9, 2013, report dated Dec. 17, 2013, 6 pgs.
Extended European Search Report for European Application No. 13852669.4, Search completed Jun. 8, 2016, dated Jun. 22, 2016, 9 pgs.
Extended European Search Report for European Application No. 14861553.7, Search completed Jun. 8 2017, dated Jun. 19, 2017, 8 Pgs.
Extended European Search Report for European Application No. 14863597.2, Search completed Jun. 6, 2017, dated Jun. 13, 2017, 9 pgs.
Extended European Search Report for European Application No. 13853514.1, Search completed Jun. 8, 2016, dated Jun. 15, 2016, 07 pgs.
International Preliminary Report on Patentability for International Application No. PCT/AU2012/001441, Report dated May 27, 2014, 10 pgs.
International Search Report and Written Opinion for International Application No. PCT/AU2011/001127, date completed Nov. 11, 2011, dated Nov. 15, 2011, 13 pgs.
International Search Report and Written Opinion for International Application No. PCT/AU2012/001441, International Filing Date Nov. 23, 2012, Search Completed Feb. 26, 2013, dated Feb. 26, 2013, 14 pgs.
International Search Report and Written Opinion for International Application No. PCT/AU2014/001049, Search completed Feb. 10, 2015, dated Feb. 10, 2015, 8 pgs.
International Search Report and Written Opinion for International Application No. PCT/AU2014/050369, Search completed Feb. 20, 2015, dated Feb. 20, 2015, 14 pgs.
International Search Report and Written Opinion for International Application No. PCT/AU2015/050135, Search completed Jun. 30, 2015, dated Jun. 30, 2015, 26 Pgs.
International Search Report and Written Opinion for International Application No. PCT/AU2015/050422, Search completed Oct. 14, 2015, dated Oct. 14, 2015, 17 pgs.
International Search Report and Written Opinion for International Application No. PCT/AU2015/050724, Search completed May 9, 2016, dated May 9, 2016, 8 Pgs.
International Search Report and Written Opinion for International Application No. PCT/AU2015/050753, Search completed Feb. 10, 2016, dated Feb. 10, 2016, 10 pgs.
International Search Report and Written Opinion for International Application No. PCT/AU2015/050787, Search completed Mar. 16, 2016, dated Mar. 16, 2016, 10 pgs.
International Search Report and Written Opinion for International Application No. PCT/AU2016/050019, Search completed May 4, 2016, dated May 4, 2016, 16 pgs.
International Search Report and Written Opinion for International Application No. PCT/AU2015/050215, Search completed Jul. 30, 2015, dated Jul. 30, 2015, 8 pgs.
International Search Report for Australian Application 2011901829 Search Completed Feb. 6, 2012, dated Feb. 7, 2012, 3 pgs.
International Search Report for International Application No. PCT/AU2012/000511, International Filing Date May 11, 2012, Search Completed May 17, 2012, dated May 18, 2012, 4 pgs.
International Search Report for International Application No. PCT/AU2012/000512, International Filing Date May 11, 2012, Search Completed Jul. 10, 2012, dated Jul. 11, 2012, 4 pgs.
International Search Report for International Application No. PCT/AU2012/000513, International Filing Date May 11, 2012, Search Completed May 29, 2012, dated May 30, 2012, 5 pgs.
International Search Report for International Application No. PCT/AU2012/000515, International Filing Date May 11, 2012, Search Completed May 21, 2012, dated Jun. 4, 2012, 5 pgs.
International Search Report for International Application No. PCT/AU2012/000516, International Filing Date May 11, 2012, Search Completed Jul. 11, 2012, dated Jul. 12, 2012, 8 pgs.
International Search Report for International Application No. PCT/AU2012/000517, International Filing Date May 11, 2012, Search Completed Jun. 4, 2012, dated Jun. 6, 2012, 3 pgs.
International Search Report for International Application No. PCT/AU2012/000518, International Filing Date May 11, 2012, Search Completed Jun. 8, 2012, dated Jun. 12, 2012, 4 pgs.
Medtronic, Spinal Cord Stimulation, RestoreSensor Neurostimulator, Features and Specification: Specification, Printed Jun. 16, 2014, 2 pgs.
Medtronic, Spinal Cord Stimulation, RestoreSensor Neurostimulator, Features and Specification: Summary Printed Jun. 16, 2014, 1 pg.
Written Opinion for International Application No. PCT/AU2012/000511, International Filing Date May 11, 2012, Search Completed May 17, 2012, dated May 18, 2012, 5 pgs.

(56) References Cited

OTHER PUBLICATIONS

Written Opinion for International Application No. PCT/AU2012/000512, International Filing Date May 11, 2012, Search Completed Jul. 10, 2012, dated Jul. 11, 2012, 7 pgs.
Written Opinion for International Application No. PCT/AU2012/000513, International Filing Date May 11, 2012, Search Completed May 29, 2012, dated May 30, 2012, 10 pgs.
Written Opinion for International Application No. PCT/AU2012/000515, International Filing Date May 11, 2012, Search Completed May 21, 2012, dated Jun. 4, 2012, 4 pgs.
Written Opinion for International Application No. PCT/AU2012/000516, International Filing Date May 11, 2012, Search Completed Jul. 11, 2012, dated Jul. 12, 2012, 8 pgs.
Written Opinion for International Application No. PCT/AU2012/000517, International Filing Date May 11, 2012, Search Completed Jun. 4, 2012, dated Jun. 6, 2012, 5 pgs.
Written Opinion for International Application No. PCT/AU2012/000518, International Filing Date May 11, 2012, Search Completed Jun. 8, 2012, dated Jun. 12, 2012, 10 pgs.
Medtronic, RestoreSensor Neurostimulator, Retrieved from: http://web.archive.org/web/20150328092923/http://professional.medtronic.com: 80/pt/neuro/scs/prod/restore-sensor/features-specifications/index.htm, Capture Date Jul. 9, 2012, Printed on May 11, 2017.
"Advanced Pain Therapy using Neurostimulation for Chronic Pain", Medtronic RestoreSensor clinical trial paper,Clinical summary, Nov. 2011, pp. 32.
"Battelle Neurotechnology—Moving Beyond the Limits in Neurotechnology", Battelle, www.battelle.org, May 2014, pp. 1-2.
"Haptic technology", Wkipedia, Retrieved from: http://en.wikipedia.org/wiki/Haptic_technology, Last modified on Sep. 15, 2014, Printed on Sep. 15, 2014, 5 pgs.
"Implants for surgery, Cardiac pacemakers", IS-1 standard ISO 5841-3-2000, Oct. 15, 2000.
International Search Report & Written Opinion for International Application No. PCT/AU2013/001280, Search Completed Jan. 16, 2014, dated Jan. 16, 2014, 8 Pgs.
International Search Report & Written Opinion for International Application PCT/AU2013/001279, Search Completed Jan. 9, 2014, dated Jan. 9, 2014, 9 Pgs.
"Neural Bypass Technology Enables Movement in Paralyzed Patient", Posted on Jul. 29, 2014, 6 a.m. in Brain chips/computer interface, pp. 1-2.
"Spinal Cord Stimulation, About Spinal Cord Stimulation", Medtronic, Retrieved from: http://professional.medtronic.com/pt/neuro/scs/edu/about/index.htm, Printed on Jun. 16, 2014, 2 pgs.
"Wide bandwidth BioAmplifier", http://www.psylab.com/html/default_bioamp.htm, Printed Jan. 30, 2014, 1-3 pages.
Andreassen, S. et al. "Muscle Fibre Conduction Velocity in Motor Units of the Human Anterior Tibial Muscle: a New Size Principle Parameter", J. Physiol, (1987), 391, pp. 561-571.
Andy, "Parafascicular-Center Median Nuclei Stimulation for Intractable Pain and Dyskinesia (Painful-Dyskinesia)", Stereotactic and Functional Neurosurgery, Appl. Neurophysiol., 43, No. 3-5, 1980, pp. 133-144.
Balzer et al., "Localization of cervical and cervicomedullary stimulation leads for pain treatment using median nerve somatosensay evoked potential collision testing", Journal of Neurosurgery, Jan. 2011, vol. 114, No. 1: pp. 200-205.
Blum, A. R., "An Electronic System for Extracelluar Neural Stimulation and Recording", Dissertation, Georgia Institute of Technology, Aug. 2007, Retrieved from http://smartech.gatech.edu/handle/1853/16192 on Jan. 30, 2012.
Borg et al., "Conduction velocity and refractory period of single motor nerve fibres in antecedent poliomyelitis", Journal of Neurology, Neurosurgery, and Psychiatry, vol. 50, 1987, 443-446.
Brown et al., "Impact of Deep Brain Stimulation on Upper Limb Askinesia in Parkinson's Disease", Annals of Neurology, 45, No. 4, 1999, pp. 473-488.
Budagavi et al., "Modelling of compound nerve action potentials health and disease", Engineering in Medicine and Biology Society, 1992 14th Annual International Conference of the IEEE. vol. 6. IEEE, 1992. pp. 2600-2601.
Coquery et al., "Backward and forward masking in the perception of cutaneous stimuli", Perception & Psychophysics, 1973, vol. 13.No. 2, pp. 161-163.
Dawson, G. D., "The relative excitability and conduction velocity of sensory and motor nerve fibres in man", Journal of Physiology, 1956, vol. 131(2), pp. 436-451. Figs. 1-5; Table 1; p. 437 "Methods"; pp. 438-447 "Results".
Devergnas et al., A "Cortical potentials evoked by deep brain stimulation in the subthalamic area", Front Syst Neurosci. 2011; 5: 30. May 13, 2011. doi:10.3389/fnsys.2011.00030.
Dijkstra, E. A., "Ultrasonic Distance Detection for a Closed-Loop Spinal Cord Stimulation System", Proceedings—19th International Conference—IEEE/EMBS Oct. 30-Nov. 2, 1997, Chicago, IL. p. 324 section 'Paraesthesia Coverage by Dermatome,' p. 326 section 'Total Paraesthesia Coverage' and Figures 1 and 6-10.
Dillier, N et al., "Measurement of the electrically evoked compound action potential via a neural response telemetry system", Ann. Otol. Rhinol. Laryngol. 111 (May 2002), No. 5, pp. 407-414. Abstract & Figures 2-3, 407-414.
Doiron et al., "Persistent Na+ Current Modifies Burst Discharge by Regulating Conditional Backpropagation of Dendritic Spikes", Journal of Neurophysiology 89, No. 1 (Jan. 1, 2003): 324-337, doi:10.1152/jn.00729.2002.
England et al., "Increased Numbers of Sodium Channels Form Along Demyelinated Axons", Brain Research 548, No. 1-2 (May 10, 1991): 334-337.
Fagius, J. et al., "Sympathetic Reflex Latencies and Conduction Velocities in Normal Man", Journal of Neurological Sciences, 1980. vol. 47, pp. 433-448.
Falowski et al., "Spinal Cord Stimulation: an update", Neurotherapeutics: The Journal of the American Society for Experimental NeuroTherapeutics 5, No. 1, Jan. 2008, pp. 86-99.
Franke et al., FELIX, "An Online Spike Detection and Spike Classification Algorithm Capable of Instantaneous Resolution of Overlapping Spikes", Journal of Computational Neuroscience, 2010, vol. 29, No. 1-2, pp. 127-148.
Fuentes et al., "Spinal Cord Stimulation Restores Locomotion in Animal Models of Parkinson's Disease", Science, vol. 323, No. 5921, Mar. 20, 2009, pp. 1578-1582.
George et al., "Vagus nerve stimulation: a new tool for brain research and therapy", Biological Psychiatry 47, No. 4, Feb. 15, 2000, pp. 287-295.
Goodall, E. V., "Modeling Study of Activation and Propagation delays During Stimulation of Peripheral Nerve Fibres with a Tripolar Cuff Electrode", IEEE Trans.Rehab.Eng. v 3, pp. 272-282.
Gorman et al., "ECAP Mapping of the Spinal Cord: Influence of Electrode Position on Aβ Recruitment", (2012). In 16th Annual Meeting. Presented at the North American Neuromodulation Society, Las Vegas, NV.
Gorman et al., "Neural Recordings for Feedback Control of Spinal Cord Stimulation: Reduction of Paresthesia Variability", 2013, In International Neuromodulation Society 11th World Congress. Presented at the International Neuromodulation Society 11th World Congress, Berlin, Germany.
Hallstrom et al, "Distribution of lumbar spinal evoked potentials and their correlation with stimulation-induced paresthesiae", (1991), Electroencephalography and clinical neurophysiology 80:126-139.
Harper, A. A. et al., "Conduction Velocity is Related to Morphological Cell Type in Rat Dorsal Root Ganglion Neurones", J. Physiol, (1985), 359, pp. 31-46.
Holsheimer et al., "Optimum Electrode Geometry for Spinal Cord Stimulation: the Narrow Bipole and Tripole", Medical and Biological Engineering and Computing, 35, No. 5, 1997, pp. 493-497.
Huff, Terry B. et al., "Real-Time CARS Imaging Reveals a Calpain-Dependent Pathway for Paranodal Myelin Retraction during High-Frequency Stimulation", PLoS ONE vol. 6, issue 3 (Mar. 3, 2011): e17176, 11 pgs.

(56) References Cited

OTHER PUBLICATIONS

Hui, Ouyang et al., "Compression Induces Acute Demyelination and Potassium Channel Exposure in Spinal Cord", Journal of Neurotrauma 27, No. 6, Jun. 2010, 1109-1120, doi:10.1089/neu.2010.1271.
Kent et al., "Instrumentation to Record Evoked Potentials for Closed-Loop Control of Deep Brain Stimulation", Conf. Proc. IEEE Eng. Med Biol. Sol, Aug. 2012, 10 pgs.
Kent et al., AR, "Recording evoked potentials during deep brain stimulation: development and validation of instrumentation to suppress the stimulus artefact", J Neural Eng. Jun. 2012; 9 (3):036004, Apr. 18, 2012. doi: 10.1088/1741-2560/9/3/036004.
Kim et al., "A Wavelet-Based Method for Action Potential Detection From Extracellular Neural Signal Recording With Low Signal-to-Noise Ratio", IEEE Transactions on Biomedical Engineering, vol. 50. No. 8, Aug. 2003.
Kim et al., "Cell Type-specific Changes of the Membrane Properties of Peripherally-axotomized Dorsal Root Ganglion Neurons in a Rat Model of Neuropathic Pain", Neuroscience 86, No. 1 (May 21, 1998): 301-309, doi:10.1016/S0306-4522(98)00022-0.
Krames et al., "Neuromodulation", 1st Edition, Academic Press, 2009, p. 540-541.
Krarup, Christian, "Compound sensory action potential in normal and pathological human nerves", Muscle & nerve, vol. 29, No. 4 (2004), pp. 465-483.
Krishnan et al., "Excitability Differences in Lower-Limb Motor Axons During and After Ischemia", Muscle & nerve, vol. 31, No. 2 (2005), pp. 205-213.
Kumar et al., "Deep Brain Stimulation for Intractable Pain: a 15-year Experience", Neurosurgery, Issue 40, No. 4, Apr. 1997, pp. 736-747.
Kumar et al., "Double-blind evaluation of subthalamic nucleus deep brain stimulation in advanced Parkinson's disease", by the American Academy of Neurology, 51, No. 3, Sep. 1, 1998, pp. 850-855.
Kumar et al., "Globus Pallidus Deep Brain Stimulation for Generalized Dystonia: Clinical and PET Investigation", Neurology, 53, No. 4, 1999, pp. 871-874.
Laird et al., "A Model of Evoked Potentials in Spinal Cord Stimulation", IEEE Engineering in Medicine & Biology Society, 35th Annual Conference. Osaka, Japan: Jul. 3-7, 2013, pp. 6555-6558.
Lempka, Scott, "The Electrode-Tissue Interface During Recording and Stimulation in the Central Nervous System", published on May 2010.
Levy et al., "Incidence and Avoidance of Neurologic Complications with Paddle Type Spinal Cord Stimulation Leads", Neuromodulation 14(15), Sep. 2011, pp. 412-422.
Li et al., S, "Resonant antidromic cortical circuit activation as a consequence of high-frequency subthalamic deep-brain stimulation", J Neurophysiol. Dec. 2007; 98(6): 3525-37. First published Oct. 10, 2007. doi:10.1152/jn.00808.2007.
Ma et al., "Similar Electrophysiological Changes in Axotomized and Neighboring Intact Dorsal Root Ganglion Neurons", Journal of Neurophysiology 89, No. 3 (Mar. 1, 2003): 1588-1602, doi:10.1152/jn.00855.2002.
Macefield, "Spontaneous and Evoked Ectopic Discharges Recorded from Single Human Axons", Muscle & Nerve 21, No. 4, Apr. 1998, pp. 461-468.
Mahnam, A et al., "Measurement of the current-distance relationship using a novel refractory interaction technique", J. Neural Eng. 6 (2009), pp. 036005 (published May 20, 2009) Abstract, Sec. 2.2 & Figure 2b, 036005.
Markandey, Vishal, "ECG Implementation on the TMS320C5515 DSP Medical Development Kit (MDK)", Texas Instruments Application Report Jun. 2010, 35 pgs.
Massachusetts Institute of Techn, "The Compound Action Potential of the Frog Sciatic Nerve", Quantitative Physiology: Cells and Tissues. Fall, 1999, Retrieved from http://umech.mit.edu/freeman/6.021J/2001/lab.pdf on May 22, 2012.

Matzner et al., "Na+ Conductance and the Threshold for Repetitive Neuronal Firing", Brain Research 597, No. 1 (Nov. 27, 1992): 92-98, doi:10.1016/0006-8993(92)91509-D.
Mcgill, Kevin et al., "On the Nature and Elimination of Stimulus Artifact in Nerve Signals Evoked and Recorded Using Surgace Electrodes", IEEE Transactions on Biomedical Engineering, vol. BME-29, No. 2, Feb. 1982, pp. 129-137.
Melzack et al., "Pain mechanisms: a new theory", Science, New York, New York, vol. 150, No. 3699, Nov. 19, 1965, pp. 971-979.
Miles et al., "An Electrode for Prolonged Stimulation of the Brain", Proc. 8th Meeting World Soc. Stereotactic and Functional Neurosurgery, Part III, Zurich, 1981, Appl. Neurophysiol, 45, 1982, pp. 449-445 1982.
Misawa et al., "Neuropathic Pain is Associated with Increased Nodal Persistent Na(+) Currents in Human Diabetic Neuropathy", Journal of the Peripheral Nervous System: JPNS, 14, No. 4 (Dec. 2009): 279-284.
Nordin et al., "Ectopic Sensory Discharges and Paresthesiae in Patients with Disorders of Peripheral Nerves, Dorsal Roots and Dorsal Columns", Pain 20, No. 3 (Nov. 1984): 231-245, doi: 10.1016/0304-3959(84)90013-7.
Oakley et al., "Spinal Cord Stimulation: Mechanisms of Action", Spine 27, No. 22, Nov. 15, 2002, pp. 2574-2583.
Oakley et al., "Transverse Tripolar Spinal Cord Stimulation: Results of an International Multicenter Study", Neuromodulation, vol. 9, No. 3, 2006, pp. 192-203.
Obradovic et al., "Effect of pressure on the spinal cord during spinal cord stimulation in an animal model", Poster, 18th Annual Meeting of the North American Neuromodulation Society, Dec. 11-14, 2014, Las Vegas.
Oh et al., "Long-term hardware-related complications of deep brain stimulation", Neurosurgery, vol. 50, No. 6, Jun. 2002, pp. 1268-1274, discussion pp. 1274-1276.
Opsommer, E. et al., "Determination of Nerve Conduction Velocity of C-fibres in Humans from Thermal Thresholds to Contact Heat (Thermode) and from Evoked Brain Potentials to Radiant Heat (CO2 Laser)", Neurophysiologie Clinique 1999, vol. 29, pp. 411-422.
Orstavik, Kristin et al., "Pathological C-fibres in patients with a chronic painful condition", Brain (2003), 126, 567-578.
Extended European Search Report for European Application No. 16802237.4, Search completed Dec. 11, 2018, dated Dec. 19, 2018, 9 Pgs.
Extended European Search Report for European Application No. 16802238.2, Search completed Oct. 17, 2018, dated Oct. 24, 2018, 8 Pgs.
International Preliminary Report for International Application No. PCT/AU2017/050647, dated Dec. 25, 2018, 8 pgs.
International Search Report and Written Opinion for International Application No. PCT/AU2017/050647, Search completed Sep. 29, 2017, dated Sep. 29, 2017, 13 Pgs.
Bahmer et al., "Application of triphasic pulses with adjustable phase amplitude ratio (PAR) for cochlear ECAP recording: I. Amplitude growth functions", Journal of Neuroscience Methods, Clinical Neuroscience, 2012, vol. 205, pp. 202-211.
Bahmer et al., "Effects of electrical pulse polarity shape on intra cochlear neural responses in humans: Triphasic pulses with cathodic second phase", Hearing Research, 2013, vol. 306, pp. 123-130.
Gnadt et al., "Spectral Cancellation of Microstimulation Artifact for Simultaneous Neural Recording In Situ", IEEE Transactions on Biomedical Engineering, Oct. 2003, Date of Publication: Sep. 23, 2003, vol. 50, No. 10, pp. 1129-1135, DOI: 10.1109/TBME.2003.816077.
Jeffrey et al., "A reliable method for intracranial electrode implantation and chronic electrical stimulation in the mouse brain", BMC Neuroscience. Biomed Central. London. GB. vol. 14. No. 1. Aug. 6, 2013 (Aug. 6, 2013) • p. 82.
Tronnier et al., "Magnetic Resonance Imaging with Implanted Neurostimulators: An In Vitro and In Vlvo Study", Jan. 1999, Neurosurgery, vol. 44(1), p. 118-125 (Year: 1999).
Extended European Search Report for European Application No. 16739680.3, Search completed Jun. 1, 2018, dated Jun. 12, 2018, 9 Pgs.

(56) References Cited

OTHER PUBLICATIONS

French et al., "Information transmission at 500 bits/s by action potentials in a mechanosensory neuron of the cockroach", Neuroscience Letters, vol. 243, No. 1-3, Feb. 1, 1998, pp. 113-116.
Herreras, "Local Field Potentials: Myths and Misunderstandings", Frontiers in Neural Circuits, Dec. 15, 2016, vol. 10, Article 1101, 16 pgs.
International Preliminary Report on Patentability for International Application No. PCT/AU2011/001127, Report dated Mar. 5, 2013, 9 pgs.
International Preliminary Report on Patentability for International Application No. PCT/AU2012/000511, Report dated Nov. 19, 2013, 6 pgs.
International Preliminary Report on Patentability for International Application No. PCT/AU2012/000512, Report dated Nov. 19, 2013, 8 pgs.
International Preliminary Report on Patentability for International Application No. PCT/AU2012/000513, Report dated Nov. 19, 2013, 11 pgs.
International Preliminary Report on Patentability for International Application No. PCT/AU2012/000515, Report dated Nov. 19, 2013, 5 pgs.
International Preliminary Report on Patentability for International Application No. PCT/AU2012/000516, Report dated Nov. 19, 2013, 9 pgs.
International Preliminary Report on Patentability for International Application No. PCT/AU2012/000517, Report dated Nov. 19, 2013, 6 pgs.
International Preliminary Report on Patentability for International Application No. PCT/AU2012/000518, Report dated Nov. 19, 2013, 11 pgs.
International Preliminary Report on Patentability for International Application No. PCT/AU2013/001279, Report dated May 12, 2015, 6 pgs.
International Preliminary Report on Patentability for International Application No. PCT/AU2013/001280, Report dated May 12, 2015, 6 pgs.
International Preliminary Report on Patentability for International Application No. PCT/AU2014/001049, Report dated May 17, 2016, 5 pgs.
International Preliminary Report on Patentability for International Application No. PCT/AU2014/050369, Report dated May 24, 2016, 8 pgs.
International Preliminary Report on Patentability for International Application No. PCT/AU2015/050135, Report dated Oct. 4, 2016, 13 pgs.
International Preliminary Report on Patentability for International Application No. PCT/AU2015/050215, Report dated Nov. 8, 2016, 4 pgs.
International Preliminary Report on Patentability for International Application No. PCT/AU2015/050422, Report dated Jan. 31, 2017, 8 pgs.
International Preliminary Report on Patentability for International Application No. PCT/AU2015/050724, Report dated May 23, 2017, 5 pgs.
International Preliminary Report on Patentability for International Application No. PCT/AU2015/050787, Report dated Jun. 13, 2017, 6 pgs.
International Preliminary Report on Patentability for International Application No. PCT/AU2016/050019, Report dated Jul. 25, 2017, 9 pgs.
International Preliminary Report on Patentability for International Application No. PCT/AU2016/050263, Report dated Oct. 10, 2017, 9 pgs.
International Type Search Report for International Application No. AU 2015902393, Search completed May 16, 2016, dated May 16, 2016, 8 Pgs.
International Preliminary Report for International Application No. PCT/AU2017/050296, dated Oct. 9, 2018, 7 Pgs.

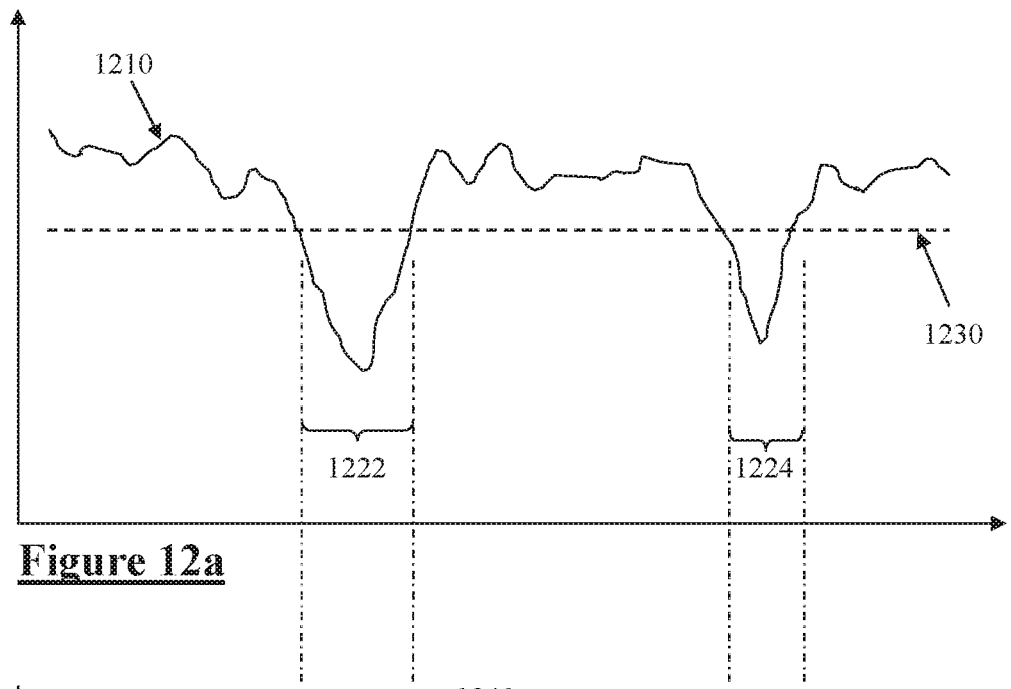
Figure 12a
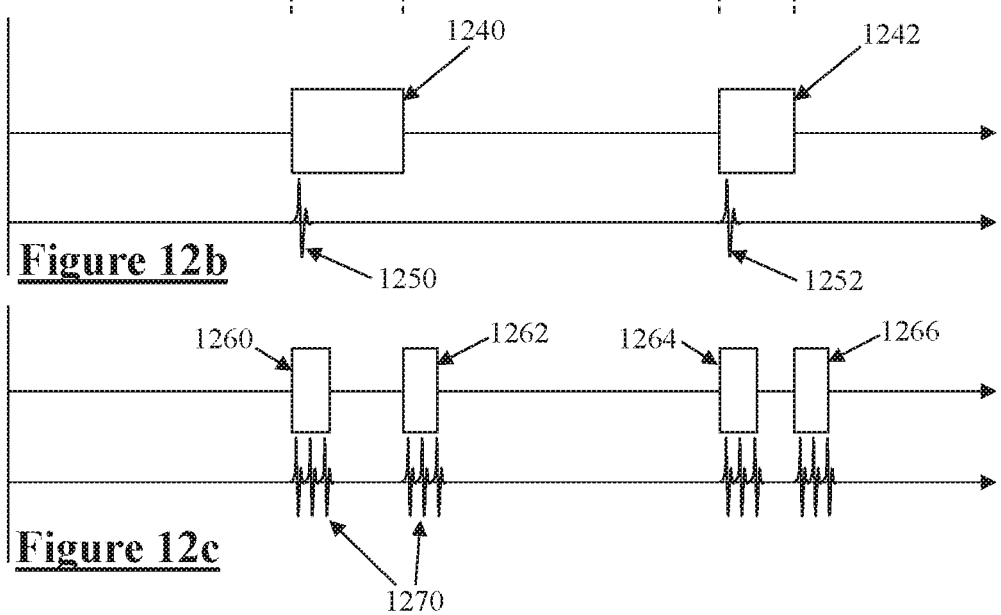
Figure 12b
Figure 12c

NEURAL STIMULATION DOSING

The current application is a 35 U.S.C. § 371 National Stage Patent Application of PCT Patent Application Serial No. PCT/AU2015/050422 entitled "Neural Stimulation Dosing" to John Louis Parker, filed Jul. 27, 2015, which application claims priority to Australian Patent Application Serial No. 2014902897, filed Jul. 25, 2014 and Australian Patent Application Serial No. 2015900912, filed Mar. 13, 2015. The disclosures of Australian Patent Application Serial Nos. 2014902897 and 2015900912 are hereby incorporated by reference in their entirety.

TECHNICAL FIELD

The present invention relates to the application of therapeutic neural stimuli, and in particular relates to applying a desired dose of stimuli by using one or more electrodes implanted proximal to the neural pathway in a variable manner to minimize adverse effects.

BACKGROUND OF THE INVENTION

There are a range of situations in which it is desirable to apply neural stimuli in order to give rise to a compound action potential (CAP). For example, neuromodulation is used to treat a variety of disorders including chronic neuropathic pain, Parkinson's disease, and migraine. A neuromodulation system applies an electrical pulse to tissue in order to generate a therapeutic effect.

When used to relieve neuropathic pain originating in the trunk and limbs, the electrical pulse is applied to the dorsal column (DC) of the spinal cord. Such a system typically comprises an implanted electrical pulse generator, and a power source such as a battery that may be rechargeable by transcutaneous inductive transfer. An electrode array is connected to the pulse generator, and is positioned in the dorsal epidural space above the dorsal column. An electrical pulse applied to the dorsal column by an electrode causes the depolarization of neurons, and the generation of propagating action potentials. The fibres being stimulated in this way inhibit the transmission of pain from that segment in the spinal cord to the brain. To sustain the pain relief effects, stimuli are applied substantially continuously, for example at a frequency in the range of 30 Hz-100 Hz.

While the clinical effect of spinal cord stimulation (SCS) is well established, the precise mechanisms involved are poorly understood. The DC is the target of the electrical stimulation, as it contains the afferent Aβ fibres of interest. Aβ fibres mediate sensations of touch, vibration and pressure from the skin.

For effective and comfortable operation, it is necessary to maintain stimuli amplitude or delivered charge above a recruitment threshold. Stimuli below the recruitment threshold will fail to recruit any action potentials. It is also necessary to apply stimuli which are below a comfort threshold, above which uncomfortable or painful percepts arise due to increasing recruitment of Aβ fibres which when recruitment is too large produce uncomfortable sensations and at high stimulation levels may even recruit sensory nerve fibres associated with acute pain, cold and pressure sensation. In almost all neuromodulation applications, a single class of fibre response is desired, but the stimulus waveforms employed can recruit other classes of fibres which cause unwanted side effects, such as muscle contraction if afferent or efferent motor fibres are recruited. The task of maintaining appropriate neural recruitment is made more difficult by electrode migration and/or postural changes of the implant recipient, either of which can significantly alter the neural recruitment arising from a given stimulus, depending on whether the stimulus is applied before or after the change in electrode position or user posture. There is room in the epidural space for the electrode array to move, and such array movement alters the electrode-to-fibre distance and thus the recruitment efficacy of a given stimulus. Moreover the spinal cord itself can move within the cerebrospinal fluid (CSF) with respect to the dura. During postural changes the amount of CSF and the distance between the spinal cord and the electrode can change significantly. This effect is so large that postural changes alone can cause a previously comfortable and effective stimulus regime to become either ineffectual or painful.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

In this specification, a statement that an element may be "at least one of" a list of options is to be understood that the element may be any one of the listed options, or may be any combination of two or more of the listed options.

SUMMARY OF THE INVENTION

According to a first aspect the present invention provides a method of applying therapeutic neural stimuli, the method comprising:

monitoring for at least one of sensory input and movement of a user; and in response to detection of at least one of sensory input and a user movement, delivering an increased stimulus dosage within a period of time corresponding to a duration of time for which the detected sensory input or user movement gives rise to masking, the increased stimulus dosage being configured to give rise to increased neural recruitment.

According to a second aspect the present invention provides a device for applying therapeutic neural stimuli, the device comprising:

at least one electrode configured to be positioned alongside a neural pathway of a user; and a control unit configured to monitor for at least one of sensory input and movement of the user, and configured to deliver, in response to detection of at least one of sensory input and a user movement, an increased stimulus dosage via the at least one electrode within a period of time corresponding to a duration of time for which the detected sensory input or user movement gives rise to masking, the increased stimulus dosage being configured to give rise to increased neural recruitment.

The first and second aspects of the present invention recognize that during movement or sensory input the psychophysics of perception can result in the individual perceiving a reduced sensation from a given stimulus as compared to when the same stimulus is applied while the individual is not moving nor receiving sensory input. However, the benefits of delivering a large dosage of stimuli remain for a period of time after conclusion of the stimuli. The first and second aspects of the present invention thus recognize that periods of time during which the user is moving or receiving sensory input present an opportunity to deliver an increased dosage of stimulation.

In some embodiments of the first and second aspects of the invention, the increased stimulus dosage may be effected by increasing one or more of the stimulus amplitude, the stimulus pulse width and/or the stimulus frequency. The increased stimulus dosage may for example comprise a burst of high frequency stimuli, for example stimuli at 10 kHz, 40 μs pulse width and 2 mA amplitude. At times when neither sensory input nor movement is detected stimuli may be delivered at a reduced dosage, for example at 20 or 30 Hz, or even not at all.

In some embodiments, a cumulative stimulus dosage delivered to the user may be monitored, and may be used as a basis to define a required stimulus regime during periods of sensory input or movement, and/or during periods of no sensory input and no movement, in order to seek to deliver a desired total stimulus dosage over the course of a dosage period such as an hour or a day.

In some embodiments, sensory input or movement of the user is detected by measuring neural activity upon the neural pathway. The measured neural activity may comprise evoked neural responses resulting from electrical stimuli applied to the neural pathway, and for example sensory input or movement may be detected when a change is detected in the neural response evoked from a given stimulus. The measured neural activity may additionally or alternatively comprise non-evoked neural activity, being the neural activity present on the neural pathway for reasons other than the application of electrical stimuli by the device. Such embodiments recognize that non-evoked neural activity rises significantly during periods of sensory input or user movement, so that an observed increase or alteration in non-evoked neural activity can be taken to indicate sensory input or user movement.

In other embodiments, movement of the user may be detected by an accelerometer or other movement detector.

The period of time within which the increased stimulus dosage is delivered may be predefined as an approximation of the duration of a typical human movement, and for example may be predefined to be of the order of one second in duration. Additionally or alternatively, the period of time for which the increased stimulus dosage is delivered may be adaptively determined by performing the further step of detecting a cessation of sensory input or movement of the user, and in turn ceasing the delivery of the increased stimulus dosage.

Additionally or alternatively, the period of time for which the increased stimulus dosage is delivered may be predefined or adaptively determined to take a value corresponding to the typical duration of non-evoked neural activity. For example, in some embodiments the period of time for which the increased stimulus dosage is delivered may be in the range 10-100 ms, or more preferably 20-40 ms, more preferably around 30 ms. In such embodiments the increase in stimulus dosage may involve imposing an increased frequency of stimulation, for example by increasing a frequency of stimulation from 60 Hz to 1 kHz in order to deliver around 30 stimuli during a 30 ms window of non-evoked neural activity rather than delivering only about 2 stimuli as would occur at 60 Hz.

Additionally or alternatively, the period of time for which the increased stimulus dosage is delivered and/or a stimulus strength of the increased stimulus dosage may be adaptively determined by performing the further step of measuring a strength of the movement or sensory input, and determining the period of time and/or the stimulus strength from the movement strength, for example the period of time and/or the stimulus strength may be made to be proportional to the movement strength. The movement or sensory strength may for example comprise a magnitude or power of the detected movement or sensory input, or other strength measure of the detected movement or sensory input. In such embodiments the stimulus strength may be controlled to remain below a threshold for sensation by a certain amount or fraction, over time as the threshold for sensation varies with movement or sensory input, to thereby avoid or minimize the stimuli causing a paraesthesia sensation while maintaining a therapeutic dose of the stimuli.

The increased stimulus dosage may be delivered throughout the period of time or at select moments within the period of time such as only at the commencement and/or cessation of the sensory input or movement or the period of time.

According to a third aspect the present invention provides a method for effecting a neural blockade, the method comprising:

delivering a sequence of electrical stimuli to neural tissue, each stimulus configured at a level whereby at least at a given relative position of a stimulus electrode to the neural tissue a first stimulus of the sequence generates an action potential and whereby each subsequent stimulus alters a membrane potential of the neural tissue without causing depolarization of the neural tissue nor evoking an action potential, each subsequent stimulus being delivered prior to recovery of the membrane potential of the neural tissue from a preceding stimulus such that the sequence of stimuli maintains the membrane potential in an altered range in which conduction of action potentials is hindered or prevented.

According to a fourth aspect the present invention provides a device for effecting a neural blockade, the device comprising:

at least one electrode configured to be positioned alongside a neural pathway of a user; and a control unit configured to deliver a sequence of electrical stimuli to neural tissue, each stimulus configured at a level whereby at least at a given relative position of the electrode to the neural tissue a first stimulus of the sequence generates an action potential and whereby each subsequent stimulus alters a membrane potential of the neural tissue without causing depolarization of the neural tissue nor evoking an action potential, each subsequent stimulus being delivered prior to recovery of the membrane potential of the neural tissue from a preceding stimulus such that the sequence of stimuli maintains the membrane potential in an altered range in which conduction of action potentials is hindered or prevented.

Embodiments of the third and fourth aspects of the invention thus apply a sequence of stimuli which at first produce an action potential and which then create a blockade, the blockade arising during the period in which the sequence of stimuli maintains the membrane potential in an altered range in which conduction of action potentials is hindered or prevented. In some embodiments a blockade may be effected by applying a sequence of supra-threshold stimuli, the first of which will evoke an action potential. Additional or alternative embodiments may effect a blockade by applying a sequence of stimuli which are sub-threshold in a first posture, but which become supra-threshold at times when the user moves to a second posture. In such embodiments, the first stimulus delivered after the stimulus threshold falls below the stimulus amplitude will evoke an action potential. Blockading is beneficial because the stimuli delivered during the blockade evoke few or no action potentials at the stimulus site and will thus give rise to a significantly reduced effect of, or even a complete absence of, paresthesia.

In some embodiments of the third and fourth aspects of the invention, the sequence of stimuli may be delivered at a frequency, or an average frequency, which is greater than 500 Hz, more preferably greater than 1 kHz, and for example may be in the range of 5-15 kHz. In some embodiments the frequency may be defined by determining an average refractory period of the subject, such as by using the techniques of International Patent Application Publication No. WO2012155189, the contents of which are incorporated herein by reference. The frequency of the delivered stimuli may then be set so that the inter-stimulus time is less than the determined refractory period, or is a suitable fraction or multiple thereof.

In some embodiments of the third and fourth aspects of the invention, the nominal sub-threshold level may be pre-determined for example by a clinician at a time of fitting of an implanted stimulator for the user. The nominal sub-threshold level is in some embodiments set at a level which is a large fraction of a stimulus threshold in a given posture, for example being 50%, 75% or 90% as large as the stimulus threshold in that posture. The nominal sub-threshold level may be adaptively determined, for example by repeatedly determining a recruitment threshold of the neural tissue from time to time, such as by measuring neural responses evoked by stimuli, and re-setting the nominal sub-threshold level by reference to a most recent determined threshold level. The recruitment threshold of the neural tissue is in some embodiments determined at time intervals which are substantially greater than the duration of a typical human movement so as to allow the neural blockade to be established during a movement.

Some embodiments of the invention may implement blockading in accordance with the third aspect of the invention only at times of detected sensory input or movement, in accordance with the first aspect of the invention. In such embodiments, the detection of sensory input or movement may be effected by delivering the blockade stimuli continuously at the nominal sub-threshold level, whereby the blockade stimuli come into effect only during sensory input or movements which cause the momentary recruitment threshold to fall below the nominal sub-threshold level. Alternatively, in such embodiments the blockading may be commenced in response to detection of sensory input or movement so that the action potential generated by the first stimulus of the sequence is masked by the sensory input or movement.

According to a fifth aspect the present invention provides a computer program product comprising computer program code means to make a computer execute a procedure for applying therapeutic neural stimuli, the computer program product comprising:

computer program code means for monitoring for at least one of sensory input and movement of a user; and computer program code means for, in response to detection of at least one of sensory input and a user movement, delivering an increased stimulus dosage within a period of time corresponding to a duration of time for which the detected sensory input or user movement gives rise to masking, the increased stimulus dosage being configured to give rise to increased neural recruitment.

According to a sixth aspect the present invention provides a computer program product comprising computer program code means to make a computer execute a procedure for effecting a neural blockade, the computer program product comprising:

computer program code means for delivering a sequence of electrical stimuli to neural tissue, each stimulus configured at a level whereby at least at a given relative position of a stimulus electrode to the neural tissue a first stimulus of the sequence generates an action potential and whereby each subsequent stimulus alters a membrane potential of the neural tissue without causing depolarization of the neural tissue nor evoking an action potential, each subsequent stimulus being delivered prior to recovery of the membrane potential of the neural tissue from a preceding stimulus such that the sequence of stimuli maintains the membrane potential in an altered range in which conduction of action potentials is hindered or prevented.

In some embodiments of the fifth and sixth aspects of the invention, the computer program product comprises a non-transitory computer readable medium comprising instructions for execution by one or more processors.

BRIEF DESCRIPTION OF THE DRAWINGS

An example of the invention will now be described with reference to the accompanying drawings, in which:

FIGS. 12a, 12b, and 12c illustrate stimulus regimes applied in accordance with some embodiments of the present invention;

DESCRIPTION OF THE PREFERRED EMBODIMENTS

Figure 1:
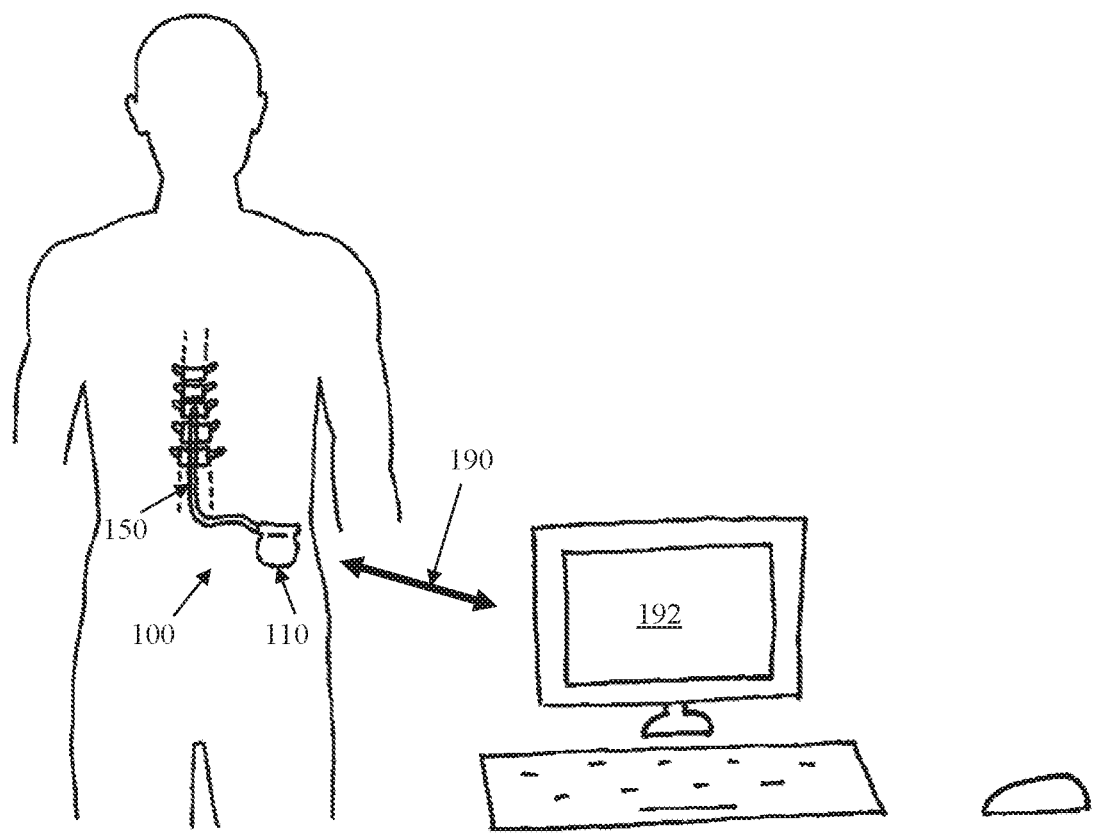
FIG. 1 schematically illustrates an implanted spinal cord stimulator.

FIG. 1 schematically illustrates an implanted spinal cord stimulator 100. Stimulator 100 comprises an electronics module 110 implanted at a suitable location in the patient's lower abdominal area or posterior superior gluteal region, and an electrode assembly 150 implanted within the epidural space and connected to the module 110 by a suitable lead. Numerous aspects of operation of implanted neural device 100 are reconfigurable by an external control device 192. Moreover, implanted neural device 100 serves a data gathering role, with gathered data being communicated to external device 192.

Figure 2:
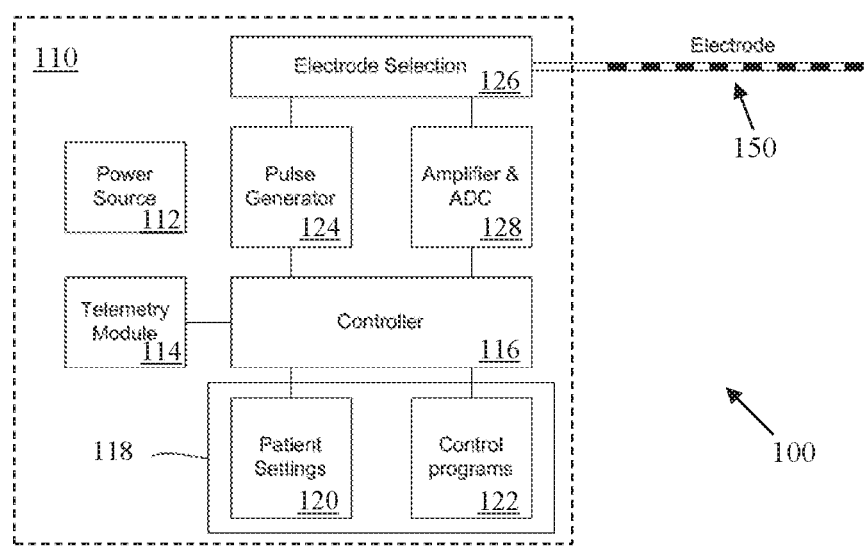
FIG. 2 is a block diagram of the implanted neurostimulator.

FIG. 2 is a block diagram of the implanted neurostimulator 100. Module 110 contains a battery 112 and a telemetry module 114. In embodiments of the present invention, any suitable type of transcutaneous communication 190, such as infrared (IR), electromagnetic, capacitive and inductive transfer, may be used by telemetry module 114 to transfer power and/or data between an external device 192 and the electronics module 110.

Module controller 116 has an associated memory 118 storing patient settings 120, control programs 122 and the like. Controller 116 controls a pulse generator 124 to generate stimuli in the form of current pulses in accordance with the patient settings 120 and control programs 122. Electrode selection module 126 switches the generated pulses to the appropriate electrode(s) of electrode array 150, for delivery of the current pulse to the tissue surrounding the selected electrode(s). Measurement circuitry 128 is configured to capture measurements of neural responses sensed at sense electrode(s) of the electrode array as selected by electrode selection module 126.

Figure 3:
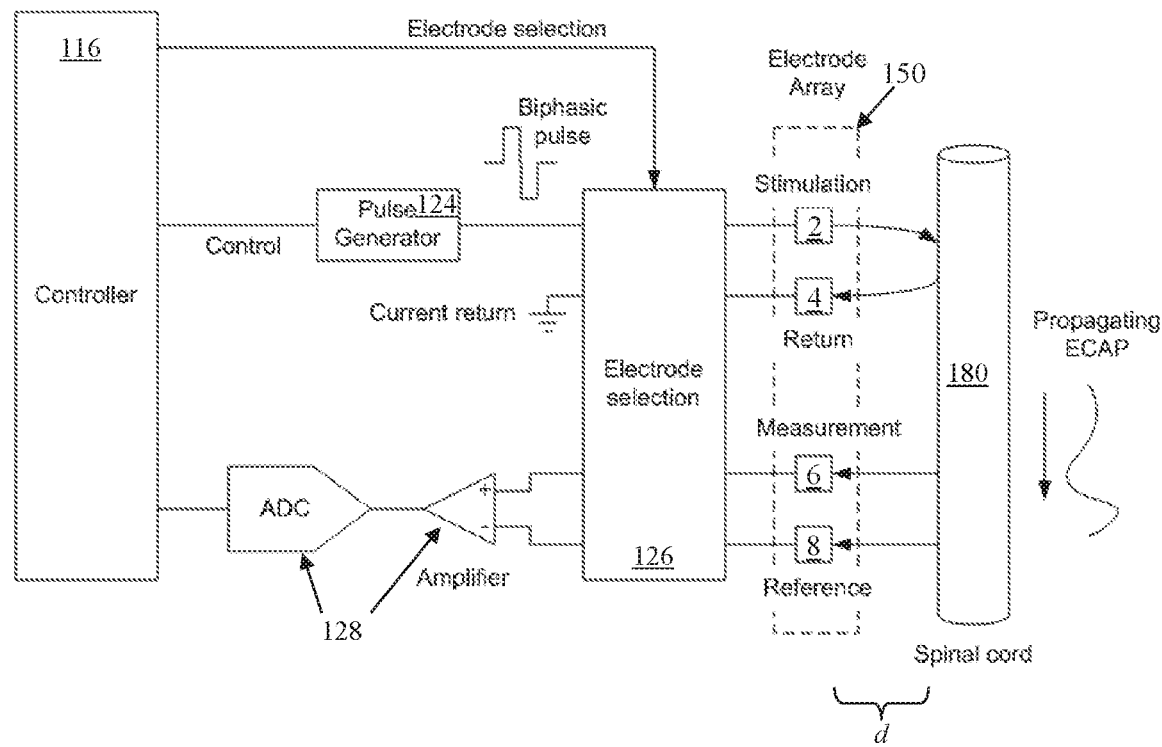
FIG. 3 is a schematic illustrating interaction of the implanted stimulator with a nerve.

FIG. 3 is a schematic illustrating interaction of the implanted stimulator 100 with a nerve 180, in this case the spinal cord however alternative embodiments may be positioned adjacent any desired neural tissue including a peripheral nerve, visceral nerve, parasympathetic nerve or a brain structure. Electrode selection module 126 selects a stimulation electrode 2 of electrode array 150 to deliver an electrical current pulse to surrounding tissue including nerve 180, and also selects a return electrode 4 of the array 150 for stimulus current recovery to maintain a zero net charge transfer.

Delivery of an appropriate stimulus to the nerve 180 evokes a neural response comprising a compound action potential which will propagate along the nerve 180 as illustrated, for therapeutic purposes which in the case of a spinal cord stimulator for chronic pain might be to create paraesthesia at a desired location. To this end the stimulus electrodes are used to deliver stimuli at 30 Hz. To fit the device, a clinician applies stimuli which produce a sensation that is experienced by the user as a paraesthesia. When the paraesthesia is in a location and of a size which is congruent with the area of the user's body affected by pain, the clinician nominates that configuration for ongoing use.

The device 100 is further configured to sense the existence and intensity of compound action potentials (CAPs) propagating along nerve 180, whether such CAPs are evoked by the stimulus from electrodes 2 and 4, or otherwise evoked. To this end, any electrodes of the array 150 may be selected by the electrode selection module 126 to serve as measurement electrode 6 and measurement reference electrode 8. Signals sensed by the measurement electrodes 6 and 8 are passed to measurement circuitry 128, which for example may operate in accordance with the teachings of International Patent Application Publication No. WO2012155183 by the present applicant, the content of which is incorporated herein by reference.

However the present invention recognizes that it is unclear whether or not the experience of paresthesia is necessary for pain reduction on an ongoing basis. Although paraesthesia is generally not an unpleasant sensation there may nevertheless be benefits in a stimulus regime which provides pain relief without the generation of sensation.

Figure 4:
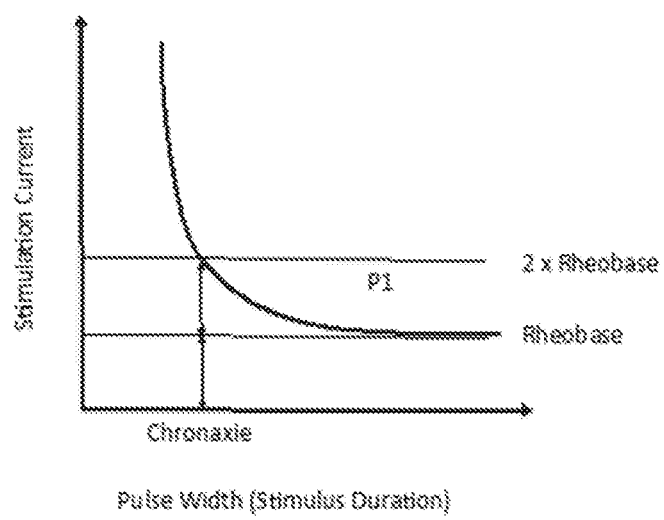
FIG. 4 illustrates the strength duration curve followed by the threshold for action potential generation in an axon.

The threshold for action potential generation in an axon follows the strength duration curve as shown in FIG. 4. As the pulse width of the stimulus is increased the current needed for an axon to reach threshold decreases. The Rheobase current is an asymptotic value, being the largest current that is incapable of producing an action potential even at very long pulse widths. The Chronaxie is then defined as the minimum pulse width required to evoke an action potential at a current that is twice the Rheobase current.

Figure 5:
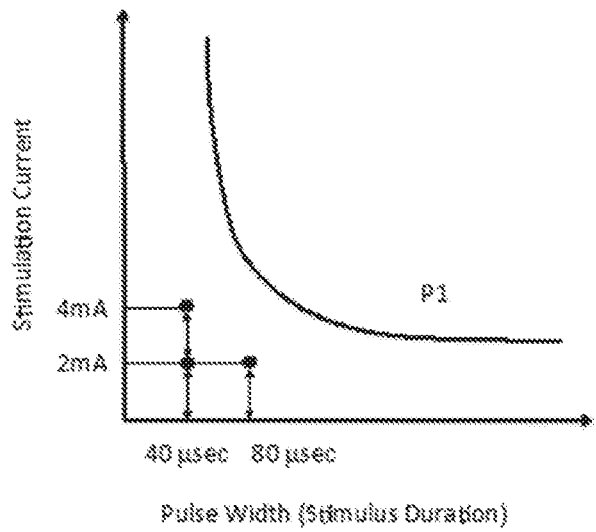
FIG. 5 illustrates the effect on the strength duration curve of delivering a high frequency pulse train.

FIG. 5 illustrates the effect on the strength duration curve of delivering a high frequency pulse train. As shown, a high frequency pulse train can effectively act as a single pulse with a longer pulse width with respect to activating a nerve. That is, closely spaced stimuli can effectively add up and recruit additional populations of fibres when compared with widely spaced stimuli with the same pulse width. Stimuli can either depolarize axon membranes to threshold and generate action potentials, or they can depolarize the axon membrane potential just below threshold and not produce an action potential. When an axon produces an action potential in response to a stimulus it is unable to produce a second potential for a period of time called the refractory period. On the other hand, those axons that did not reach threshold in response to the first stimulus may reach threshold on subsequent stimuli as their membrane potential is raised closer and closer to threshold with every stimulus, provided that the next stimuli occurs prior to recovery of the membrane potential from the previous stimuli. This effect equilibrates over a small number of high frequency stimuli, and may account for an effective doubling of the number of fibres recruited, when compared with a single stimulus of the same pulse width at low frequency.

Figure 6:
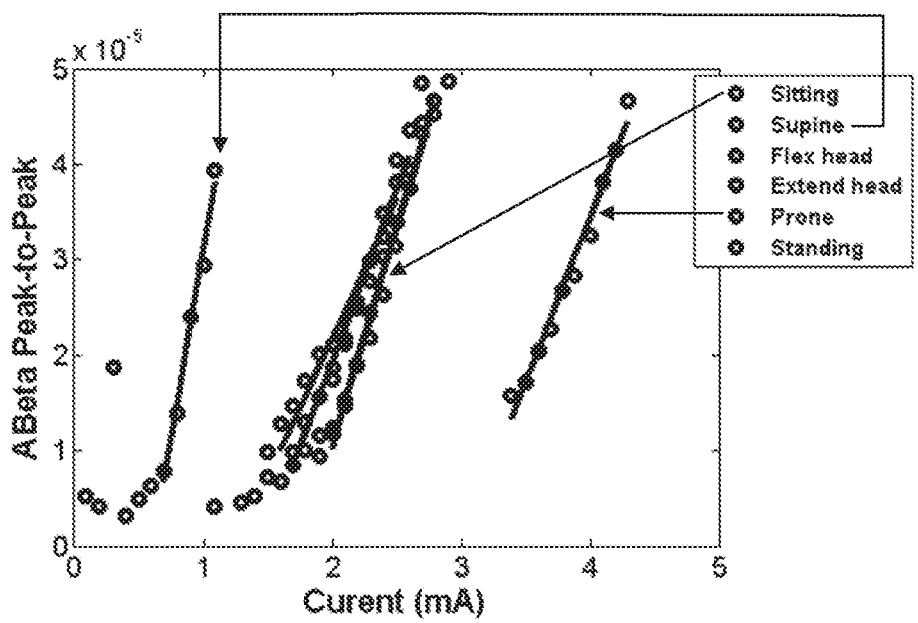
FIG. 6 shows the amplitude growth curves for an individual at a number of different postures.

Activation of Aβ fibres in the dorsal column can vary considerably in response to changes in posture. This postural affect is primarily due to the movement of the stimulus electrodes with respect to the fibres. Changes in posture can be measured by recording the evoked compound action potential (ECAP). Momentary changes in posture, for instance a sneeze or a cough, can produce a factor of 10 increase in the amplitude of an evoked CAP, or more. FIG. 6 shows the amplitude growth curves for an individual at a number of different postures. It demonstrates a significant change in recruitment threshold as the patient moves from one posture to another, with the recruitment threshold being almost as low as 0.5 mA when the user is lying supine and being about 3 mA when the user is lying prone.

Figure 7:
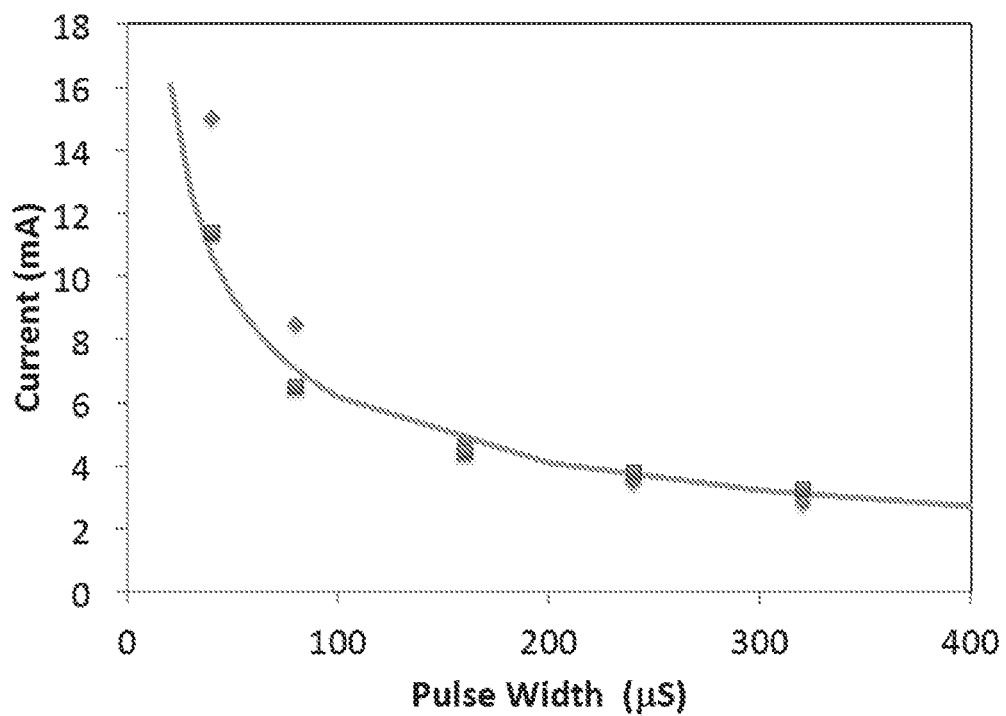
FIG. 7 shows the strength duration curve corresponding to the activation of the dorsal columns.

FIG. 7 shows the strength duration curve corresponding to the activation of the dorsal columns for a single posture. The current corresponding to the threshold for an ECAP versus the pulse width. For example a pulse width of 35 μs corresponds to a threshold current of 11.5 mA. Noting the recruitment curves of FIG. 6, when the sitting patient moves to a supine position the threshold in FIG. 7 could be expected to drop to a third of the value, which for a pulse width of 35 μs indicates that the threshold will be 11.5/3=3.83 mA. To maintain threshold in response to a change in posture, either the pulse width can be increased or as demonstrated earlier a high frequency train using a shorter pulse width could be used.

The present invention further recognizes that cutaneous sensation is suppressed by movement and by sensory input, that the level of suppression is dependent on the intensity of the movement or sensory input, and that movement induced suppression attenuates both flutter and pressure. The reduction in the pressure sensation was 30, 38 and 79% for slow, medium and rapid movement, respectively. In general, sensory input displays a masking phenomenon where the presence of a large stimulus can mask the perception of a smaller stimulus. This can even happen when the smaller stimulus is presented before the larger stimulus (forward masking). This phenomenon occurs during cutaneous input.

A first embodiment of the invention therefore provides a spinal cord stimulation system which has the ability to detect movement, and to apply or increase electrical stimulation only during the periods where movement is sufficiently strong so as to mask the sensation produced by electrical stimulation. Such a system achieves relief from pain for the individuals implanted but without generation of sensation due to the fact that the sensation which would be perceived by the subject when they are stationary is below threshold for perception during movement.

There are a number of ways in which the movement of the individual might be detected. One method is to use an accelerometer, which senses movement of the stimulator, another is to use the impedance of the electrode array which changes as a result of the motion in the epidural space of the spinal cord. A third method for detecting movement is to use the modulation of the evoked compound action potential. Closed loop neuromodulation systems have been developed which employ recordings of the compound action potential to achieve a constant recruitment, for example as described in International Patent publications WO2012155183 and WO2012155188, the contents of which are incorporated by reference in their entirety. The amplitude of the ECAP has been shown to sensitively vary with the changes in posture. The amplitude can thus be used to detect movements and time the delivery of bursts of stimuli to coincide with those movements. Measurement of the ECAP provides a method of directly assessing the level of recruitment in the dorsal columns of the spinal cord depending on posture. A further method for detecting movement, which is also suitable for detecting sensory input, is to monitor neural activity on the nerve which has not been evoked by the neurostimulator, for example in the manner described in the present applicant's Australian provisional patent application no. 2014904595, the content of which is incorporated herein by reference. Such non-evoked neural activity can result from efferent motor signals or afferent sensory or proprioceptive signals, which present opportunities at which masking can occur and thus define times at which delivery of an increased stimulus dosage may be appropriate.

Figure 8:
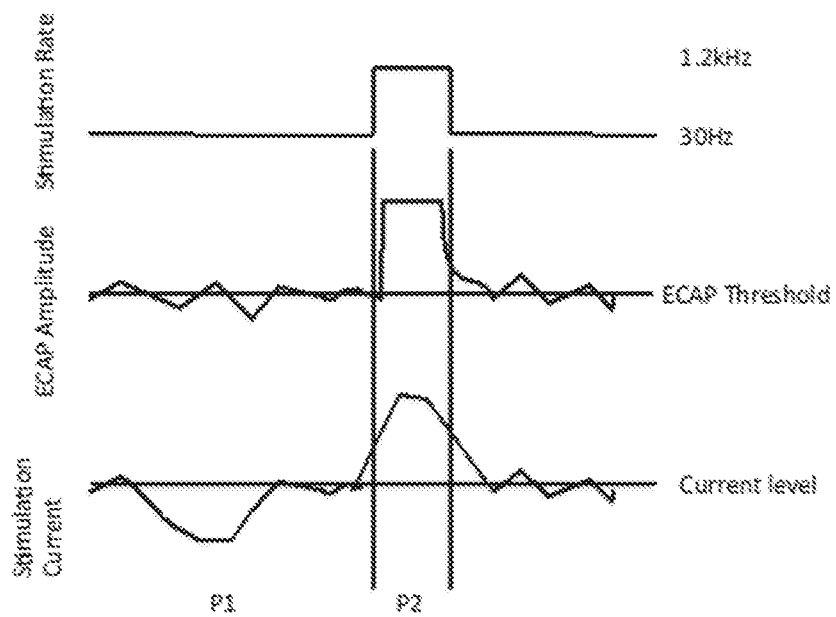
FIG. 8 illustrates monitoring of a stimulation current required to maintain a constant ECAP response.

The algorithm in this embodiment works as follows. Feedback control of a sub paraesthesia amplitude of ECAP is established with the patient stationary. Movement is detected by monitoring the stimulation current, which is constantly adjusted to maintain a constant ECAP response. A set point is established for the amplitude of the change over time which when reached indicates a sufficiently rapid movement to change stimulation parameters. A change in the current may be insufficient to meet the criteria for detecting a sufficiently large movement (as occurs in time period P1 in FIG. 8) or it may meet or exceed the criteria (as occurs in time period P2 in FIG. 8).

On detection of this change a new stimulation condition is set, by adjusting stimulation parameters. The stimulation parameters may be any of those which effect the recruitment of dorsal column fibres such as the amplitude, pulse width, stimulation frequency or combination thereof. The stimulator outputs a stimulus train at the new settings for a period of time. The output can be controlled in a feedback loop as well so that a constant level of recruitment is achieved. The timing for the increased period of stimulation is adjusted so that it ceases in a short period coincident with the movement detected, and terminates before the motion ceases, such that it is not perceived by the individual.

The timing and amplitude can be set by a number of means, such as a fixed amplitude applied for a fixed time, an amplitude which is adjusted proportionally to the amplitude of the measured ECAP or movement and terminated after a fixed interval, or a fixed amplitude of stimulation and termination after the variation, being the first derivative over time of the ECAP amplitude, drops. Recall that the stimulation parameters are adjusted on reaching a set level of variation. Thus, a fixed ECAP amplitude can be adjusted via feedback which is terminated when the 1st derivative over time of the applied current drops below a set level.

After the stimuli train is delivered the system reverts to a stimulation mode that is below perception threshold to monitor for further changes in postures, and the sequence is repeated. The adjustment of the stimulation parameters can be controlled over time (ramp up and ramp down) or other time varying function.

Without intending to be limited by theory, current postulated mechanisms of action of SCS are based on the Aβ fibre activity in the dorsal column resulting, via synaptic transmission, in the release of GABA, an inhibitory neurotransmitter, in the dorsal horn. GABA then reduces spontaneous activity in wide dynamic range neurons and hence produces pain relief. The kinetics of GABA mediated inhibition are unknown, however there is a post switch off effect from SCS which can be quite prolonged in some patients. This suggests that build-up of GABA may be possible over short periods, which would lead to longer term pain inhibition. If the quanta for GABA release is proportional to the stimuli then it is instructive to compare tonic continuous stimulation to bursts of higher frequency stimulation. Continuous tonic stimulation provides 216 000 stimuli over a one hour period at a stimulation frequency of 60 Hz, whereas at 1.2 kHz delivery of the same number of stimuli is achieved in three minutes. Given control over stimulus delivery as described above then 3 minutes of activity in an hour would result in the same number of supra-threshold stimuli delivered with tonic stimulation. Hence a higher frequency stimulus burst may be as efficacious as tonic stimulation but with a much shorter elapsed duration of stimuli.

The use of ECAPS allows the dosage of stimuli applied to the recipient during the day to be carefully controlled and additional stimuli could be applied if the number of stimuli falls below a target level which is required to achieve optimal therapy. This may occur because an individual is not active enough, or because the system set points are not optimally adjusted. Given such conditions the system can alert the user or the clinician or even revert to periods of tonic continuous super threshold stimulation.

In some embodiments the applied therapeutic stimuli may be supra threshold stimuli for neural activation, however in other embodiments sub threshold stimuli may be applied for psychophysical perception in other therapeutic areas.

Figure 9:
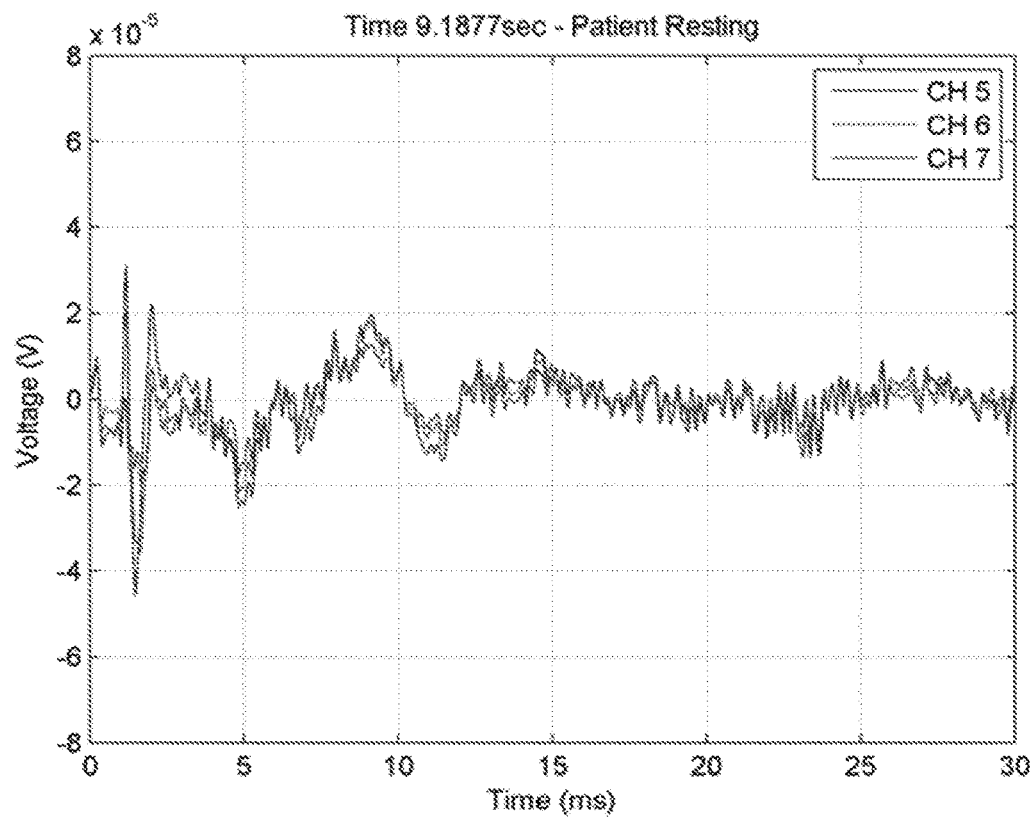
FIG. 9 show examples of ECAP recordings with a patient at rest.

ECAP measurements as described above may be used as a method to time the application of pain relieving stimuli to coincide with detected movement. A number of other methods may also be used including a measure of the patient's own non-evoked neural activity. FIG. 9 show examples of ECAP recordings with a patient at rest and FIG. 10 shows ECAP recordings with the patient walking on the spot.

Figure 10:
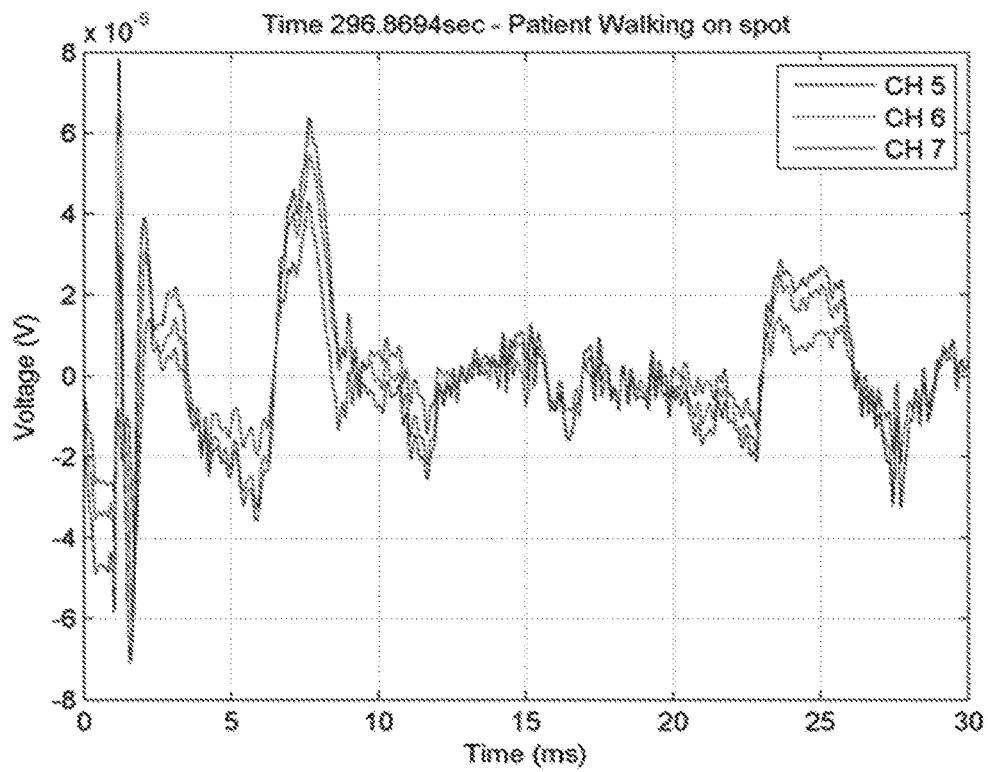
FIG. 10 shows ECAP recordings with the patient walking on the spot.

In FIGS. 9 and 10 there is a significant difference in the amplitude of the noise due to non-evoked activity immediately post the stimulus with the patient walking on the spot. Simple visual inspection shows that in FIG. 9 during the time period 15-20 s the neural activity amplitude is generally less than 5 microvolts, whereas during the same period in FIG. 10 the neural activity amplitude often exceeds 10 microvolts. A number of automated techniques may be used to determine the amplitude of the non-evoked neural activity. The amplitude can be directly measured by determining the maximum and minimum values of the response or alternatively the RMS (root mean square) can be determined over a window.

The non-evoked activity can be measured on a continuous basis without outputting stimuli. In this manner the extent of activity or movement of the individual can be assessed on a continuous basis, so that sufficiently swift movements can be detected and used as triggers for increased stimulus dosing.

Figure 11A:
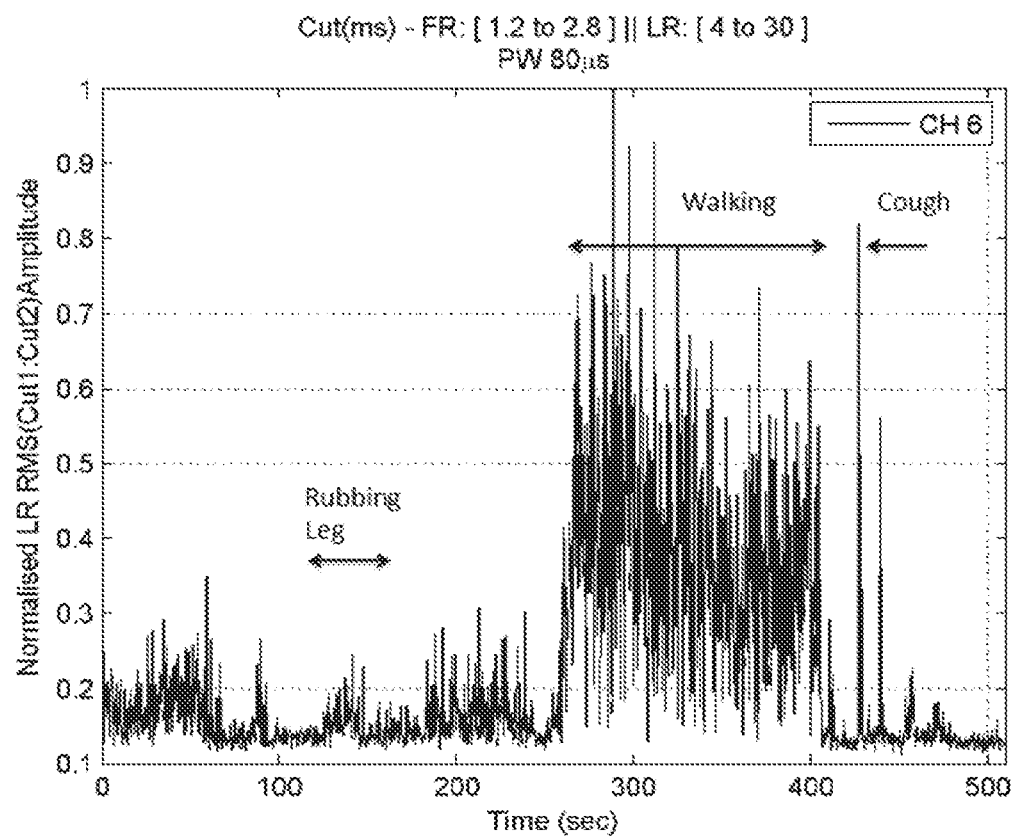
FIGS. 11a and 11b show non evoked activity measured from a patient.
Figure 11B:
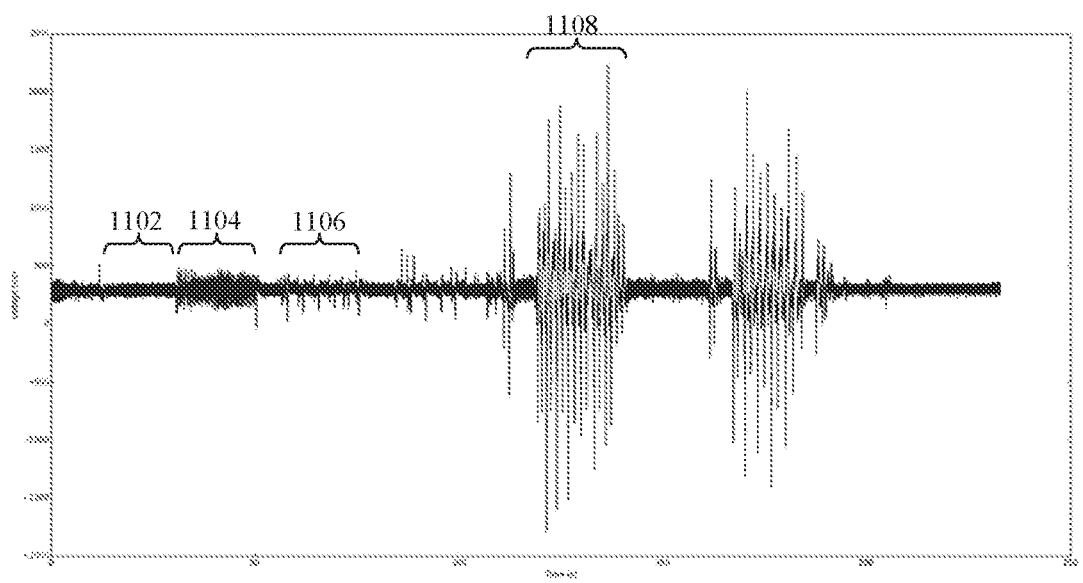

FIG. 11a shows non evoked activity measured from a patient, and shows the RMS non-evoked activity for an individual undergoing a range of movement activities from rubbing the leg to walking on the spot and coughing. As is evident in the figure the RMS signal is much larger when the patient is active and walking on the spot. FIG. 11b is another illustration of non-evoked neural activity measured from a patient, and shows the RMS non-evoked activity for an individual whom at 1102 is not moving, at 1104 is rubbing their leg, at 1106 is lifting one leg while seated and at 1108 is walking. In particular FIG. 11b shows that sensory input of rubbing the leg at 1104, and motor and/or proprioceptive input of lifting the leg at 1106, are each only subtly different from times of no movement as shown at 1102, and some embodiments of the present invention are specifically configured to address this problem.

In one embodiment, an algorithm which exploits the non-evoked activity operates as follows:
i. The implant system monitors the non-evoked activity (N) until a threshold measure of activity is reached ($T_{nn}$).
ii. On reaching the threshold, stimuli are generated and, after any evoked response has concluded, the magnitude of the post-stimulus non-evoked activity is re-measured ($N_s$).
iii. Stimuli are generated at a rate ($R_s$) until the non-evoked activity ($N_s$) falls below a second threshold measure of activity ($T_{ns}$) at which point stimulation ceases. $T_{ns}$ typically takes a smaller value than $T_{nn}$, selected to provide a suitable degree of hysteresis.
iv. The implant system then continues to monitor the non-evoked activity and returns to step (i).

The stimulus rate ($R_s$) may be a fixed rate or it may also be set to vary with the magnitude of the non-evoked activity The amplitude of the evoked activity can be used to control the amplitude of the stimulus generated with each successive stimuli in a feedback loop as has been described in International Patent Publication No. WO2012155188, for example. The advantage of employing a feedback loop in such a manner is to keep the ECAP amplitude constant during a period of active movement during which it is known to vary considerably.

The parameters for this algorithm can be determined in the following manner
i. The patient is programmed with a traditional method with continuous stimulation with patient at rest. The stimulus location and amplitude is adjusted in order to obtain paraesthesia coverage of the pain full area. The amplitude of the ECAP ($E_a$) for obtaining pain relief is noted.
ii. The stimulation is turned off and the range of non-evoked activity is measured. The threshold $T_{nn}$ is set such that it is above the base line of non-evoked activity with the patient at rest.

The presence of the non-evoked activity is the result of movement of and/or sensory input to the individual. Movement also affects the amplitude of the evoked activity, so that if the evoked activity is controlled with a feedback loop, then a change in the current or other stimulus parameter which is set to maintain a constant amplitude can be used to monitor for a change in movement and set the point for cessation of the stimuli.

By delivering increased stimuli only at times at which movement and/or sensory input is detected, the present invention provides for a considerably reduced power budget. For example if movement is detected every 15 seconds, and the delivered stimulus comprises 5 stimuli, the system will deliver 20 stimuli per minute as compared to 1200 stimuli per minute for a continuous 20 Hz stimulus regime, i.e. 98.3% fewer stimuli.

FIG. 12a illustrates the threshold 1210 of dorsal column activation, which varies over time for example with postural changes. At times 1222, 1224 this threshold 1210 drops below the stimulus level 1230. The present invention may initiate or increase the stimulus regime during these periods 1222, 1224, either throughout the entire period as shown in FIG. 12b or for example at the start and/or finish of the period as shown in FIG. 12c. It is to be noted that each affected fibre will also respond in a corresponding manner albeit at slightly different times depending on the distance of the electrode from that fibre and the time at which the user movement causes the fibre to come within the effective stimulus range of the electrode. The delivered stimuli 1240, 1242 delivered in FIG. 12b comprise a burst of high frequency stimuli at 10 kHz, 40 μs pulse width and 2 mA amplitude. Such stimuli are configured to effect a blockade during respective time periods 1222 and 1224, so that in FIG. 12b only a single action potential 1250, 1252 is produced in each time period 1222, 1224 and the fibre is then blockaded for the remainder of the respective time period.

In FIG. 12c an alternative stimulus regime is applied, with stimuli being applied only at threshold crossings, these being the moments at which the user is actually moving from one posture to the next. In accordance with the first aspect of the invention, the sequences of stimuli 1260, 1262, 1264, 1266 deliver an increased stimulus dosage during times of movement, so that an increased number of action potentials 1270 are evoked at such times. This embodiment recognizes that, during movement, the psychophysics of perception can result in the individual perceiving a reduced sensation from a given stimulus as compared to when the same stimulus is applied while the individual is not moving. However, the benefits of delivering a large dosage of stimuli remain for a period of time after conclusion of the stimuli.

Figure 13:
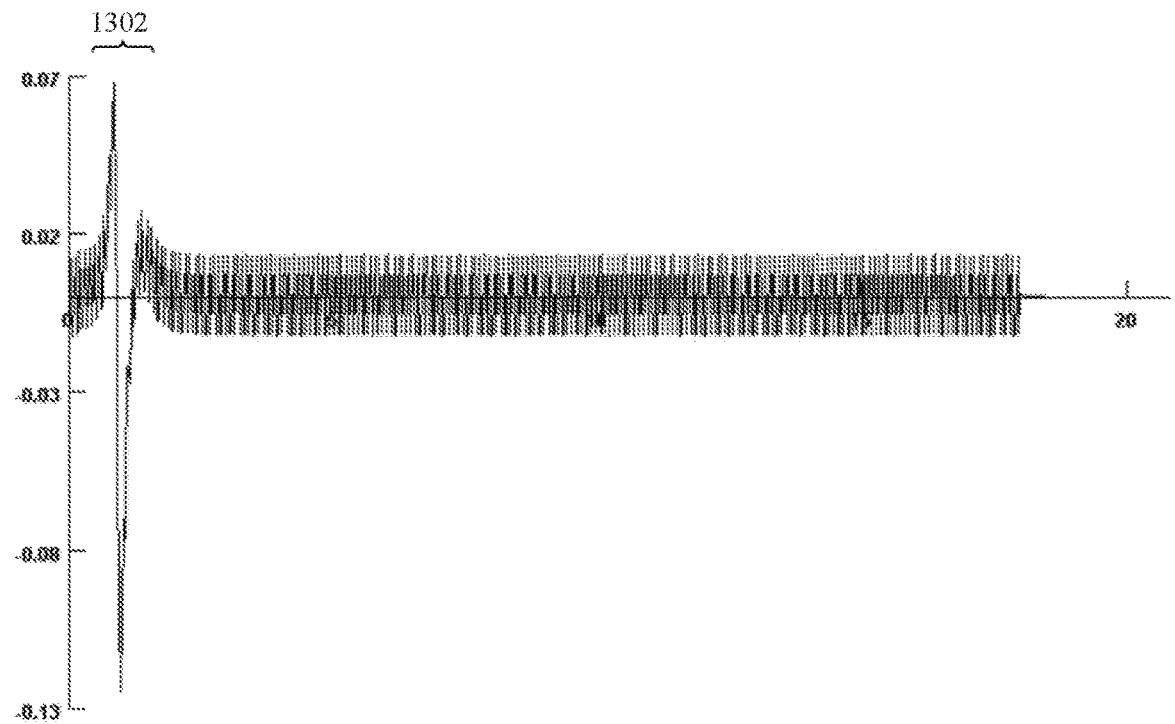
FIG. 13 illustrates the neural voltage recorded during a blockade.
Figure 14:
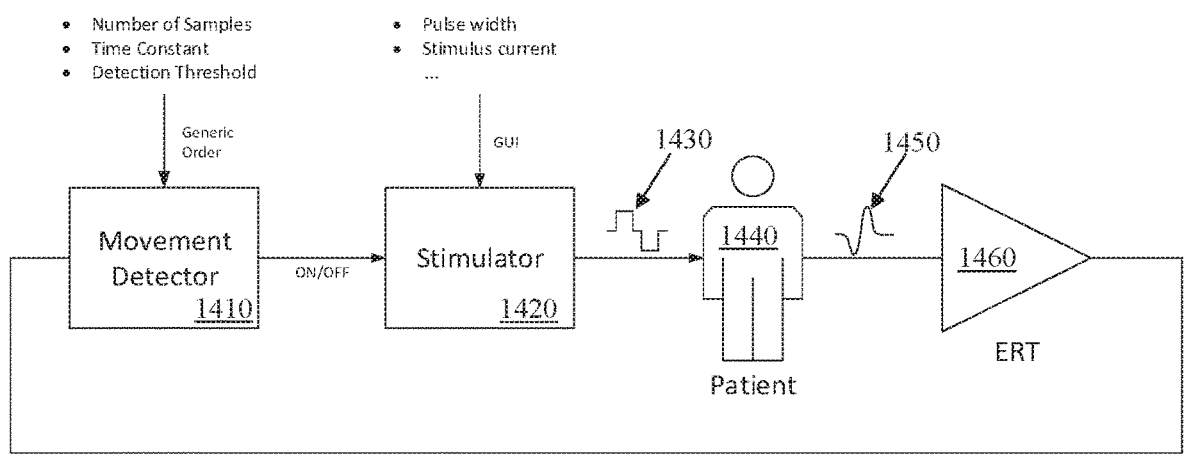
FIG. 14 illustrates operation of a motion activity detector.

FIG. 13 illustrates the neural voltage recorded during a blockade as may be produced by stimuli 1240, 1242. As can be seen the period of the high frequency sequence of stimuli is less than the period of the action potential 1302. Thus, while a first stimulus of the sequence generates action potential 1302, each subsequent stimulus alters a membrane potential of the neural tissue without causing depolarization of the neural tissue and without evoking an action potential, each subsequent stimulus being delivered prior to recovery of the membrane potential of the neural tissue from a preceding stimulus.

FIGS. 14-17 illustrate operation of a motion activity detector 1410 which detects movement of a patient 1440 by analysis of observed neural responses 1450 evoked by applied stimuli 1430. The algorithm performed by detector 1410 enables stimulation to be delivered only when movement-related slow spinal cord potentials are recorded, and otherwise disables stimulation. Movement-related spinal cord potentials are defined in this embodiment as signals greater than 200 $\mu V_{p-p}$, normalized for lead position, with a band width between 1 and 30 Hz.

One goal of the detector 1410 is to accurately detect movement of the particular limb or part of the body associated with the area that pain occurs, e.g. for leg pain the detector 1410 seeks to detect walking, lifting the leg, and the like. The detector 1410 is also configured to detect movement quickly enough to be able to commence stimulation while the movement is still occurring. The detector 1410 is also parameterized, so that the algorithm can be made to work for patients with varying stimulation parameters.

The detector 1410 operates by applying a sequence of stimuli over time and obtaining a neural response amplitude measurement after each stimuli. The sequence of neural response amplitudes obtained in this manner over the course of 30 seconds is plotted at 1502 in FIG. 15. During this period the patient was walking on the spot. The neural response signal 1502 is low pass filtered, differentiated, and rectified, to produce rectified differentiated neural response signal 1504. The differentiator allows movements to be detected early, and the rectifier ensures that both negative and positive-going signals are captured. The gradient value m[n], i.e. signal 1504, is then fed to an envelope detector with the following equation:

$$l[n] = \begin{cases} m[n], & m[n] > l[n-1] \\ \alpha l[n-1] + (1-\alpha)m[n-1], & m[n] \leq l[n-1] \end{cases}$$

Figure 15:
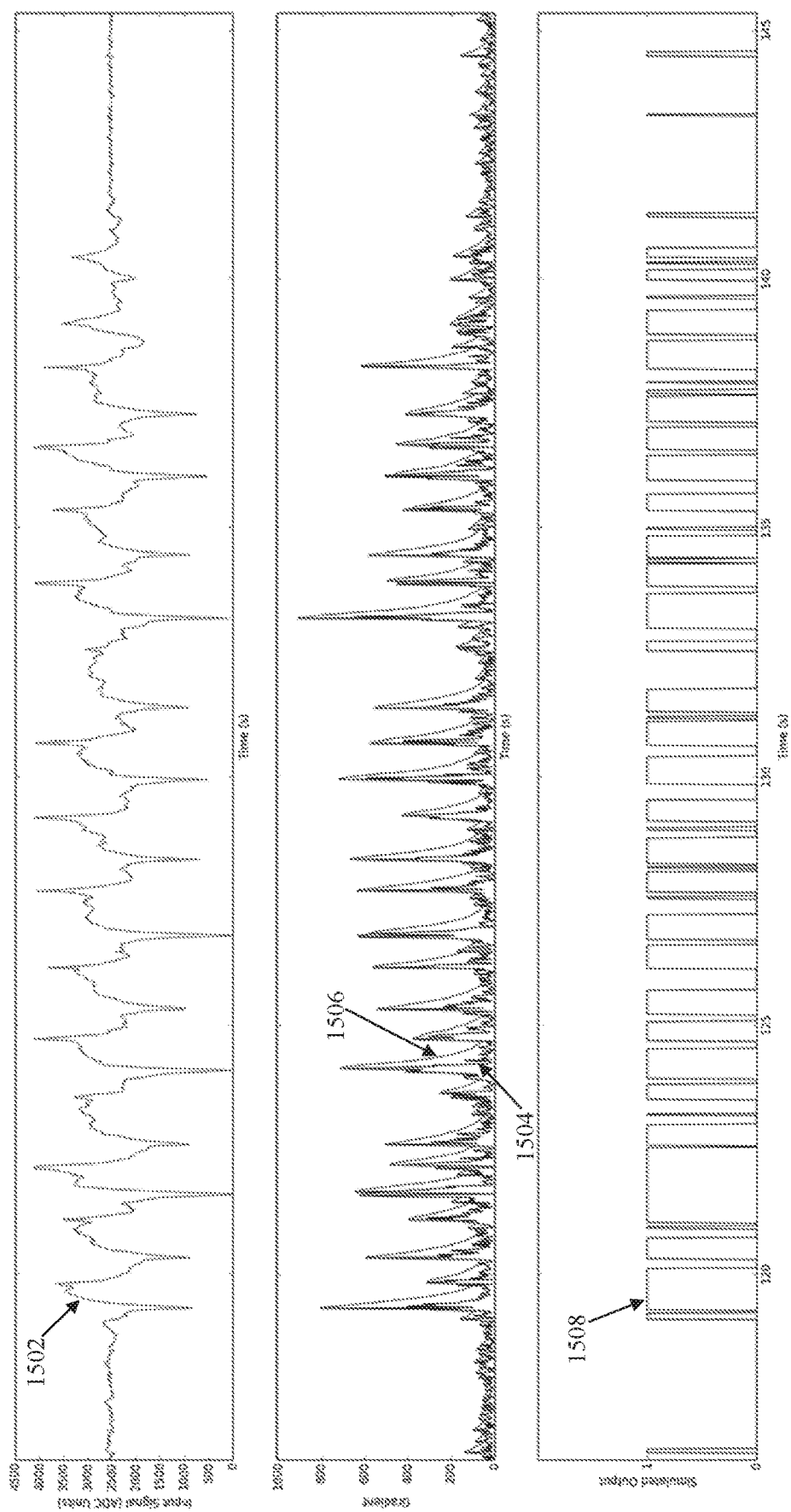
FIGS. 15-17 illustrate neural response signals observed during patient movement, and the resulting stimuli regimes delivered by the detector of FIG. 14.

The parameter a is a value between 0 and 1. Values closer to one will cause a slower envelope delay and thus cause the stimulus to be applied for a longer period after each detection. The envelope 1506 produced in the above manner from the differentiated signal 1504 is shown in FIG. 15. The detector output 1508 is thresholded from envelope 1506, where a detector output value of 1 causes stimuli to be applied, and an output of zero disables stimuli delivery. As can be seen in this embodiment, the detector output 1508 thus causes stimuli to be selectively delivered only at times when movement is detected.

Figure 16:
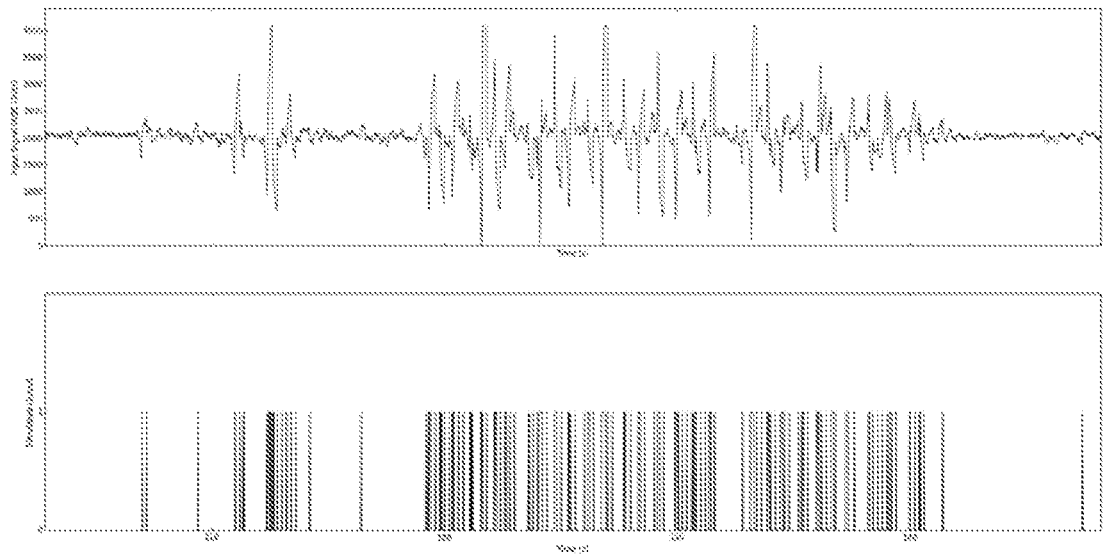
Figure 17:
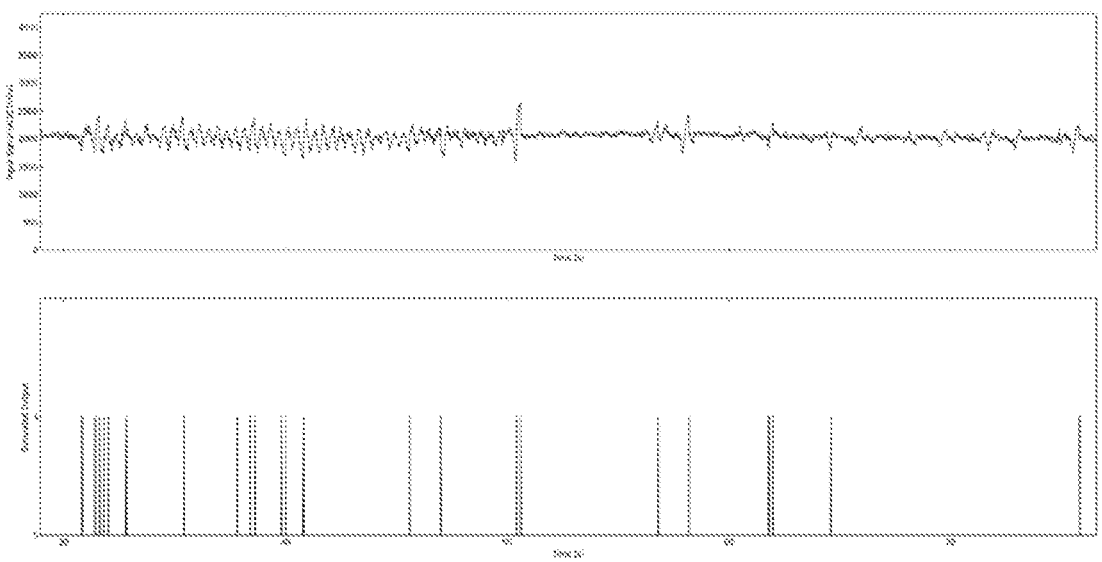

Tuning of the threshold and the parameter a allows the stimulus dosing to be adjusted. For example FIGS. 16 and 17 show the algorithm output during various patient movements with parameters which give rise to smaller or more sparse periods of stimulation than seen in 1508 in FIG. 15.

Other embodiments of the activity detector may also provide a movement magnitude output, indicating the magnitude of the movement, which may be used to modulate the magnitude or duration of the stimulation, or other stimulation parameters.

Figure 18:
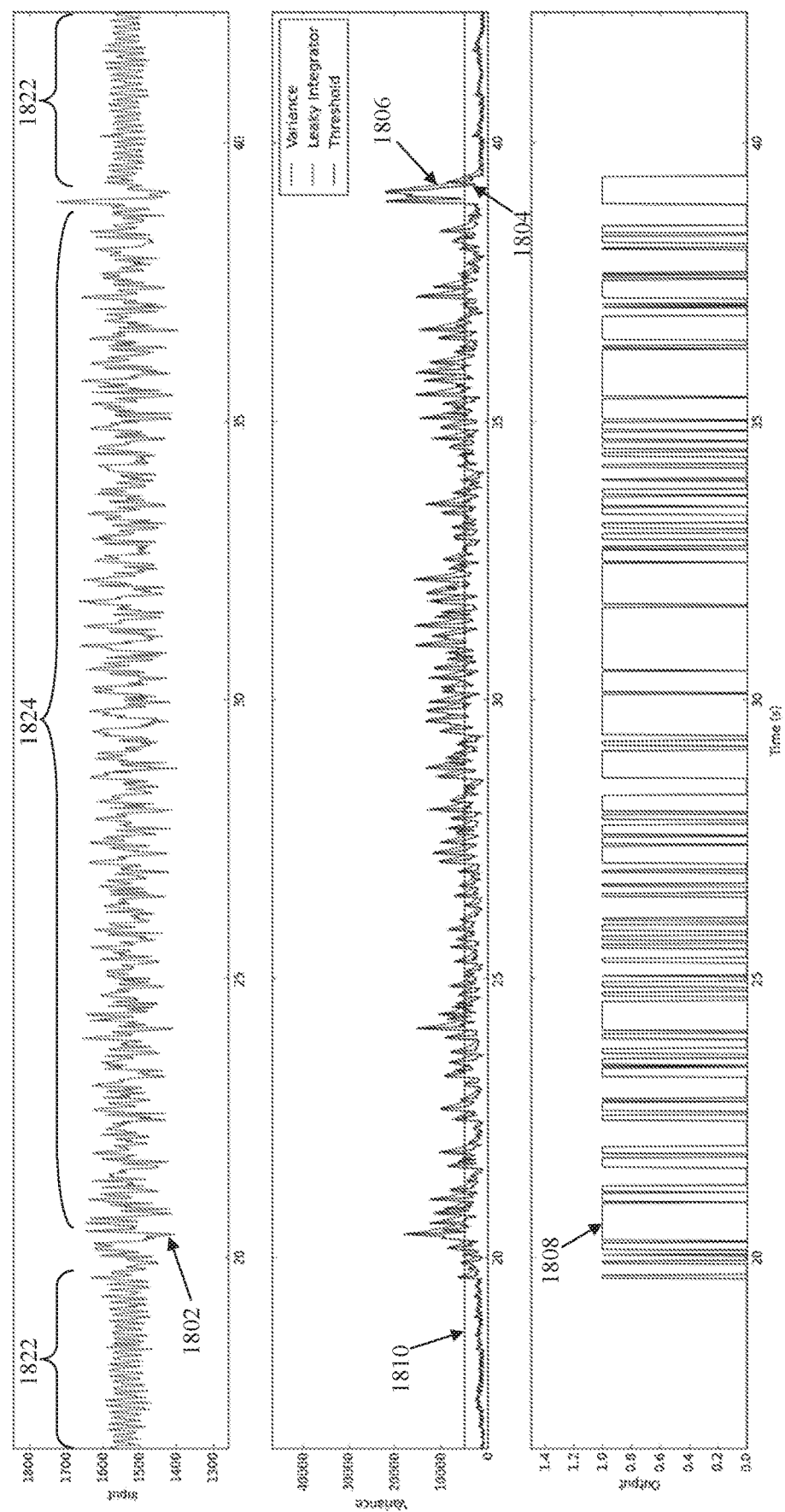
FIG. 18 illustrates operation of a neural activity detector in accordance with another embodiment of the present invention.

As can be seen the embodiment of FIGS. 14-17 is effective for periods when the patient is walking. FIG. 18 illustrates another embodiment which is further operable to appropriately detect sensory input such as rubbing the leg. In this embodiment, the detector operates by applying a sequence of stimuli over time and obtaining a neural response amplitude measurement after each stimuli. The sequence of neural response amplitudes obtained in this manner over the course of about 30 seconds is plotted at 1802 in FIG. 18. Prior to about 19 seconds into the measurements, and after about 39 seconds of measurements 1802, the patient was inactive as indicated by 1822. During period 1824 the patients rubbed their leg. The difference in signal 1802 between period 1822 and 1824 is fairly subtle, however the sensory input of leg rubbing presents an opportunity to deliver stimuli during period 1824 in order to take advantage of masking. Therefore the present embodiment is configured to analyses the measurements signal 1802 and to differentiate a period of sensory input 1824 from periods 1822 of inactivity.

To achieve this goal, the embodiment of FIG. 18 obtains the neural measurements 1802 at 60 Hz. Each measurement, or sample x[n], is saved to a circular buffer of a length defined by a Detection Window Length parameter, N. Each new sample is used to update a moving average using the formula:

$$avg[n] = \tfrac{1}{2} avg[n-1] + \tfrac{1}{2} x[n]$$

The two-sample moving average is beneficial in minimizing processing time. Next, the variance 1804 of the signal 1802 is calculated from all the samples in the circular buffer, and using the above-noted moving average:

$$\text{var}[n] = \frac{1}{N} \sum_{i=0}^{N-1} (x[n-i] - avg[n])^2$$

The variance 1804, var[n], is then fed to an envelope detector with the following equation:

$$l[n] = \begin{cases} \text{var}[n], & m[n] > l[n-1] \\ (1-\alpha)l[n-1] + \alpha \text{var}[n], & m[n] \leq l[n-1] \end{cases}$$

The parameter a is a value between 0 and 1, and can be adjusted whereby smaller values will cause the stimulus to be applied for a longer period after an initial detection. The output of the envelope detector is shown at 1806 in FIG. 18.

The detector output 1808 is produced by being thresholded from envelope 1806 by comparison to threshold 1810, where a detector output value of 1 causes stimuli to be applied, and an output of zero disables stimuli delivery. The threshold can be adjusted to suit given hardware and/or a given patient. As can be seen in this embodiment, the detector output 1808 thus causes stimuli to be selectively delivered only at times when sensory input is occurring. In particular, in this embodiment the detector output 1808 appropriately disables stimuli during period 1822, while taking good advantage of the masking opportunity afforded by leg rubbing during period 1824 to deliver an increased dosage of stimulation, despite the somewhat subtle differences in signal 1802 between the periods of inactivity 1822 and the period of leg rubbing 1824.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not limiting or restrictive.

The invention claimed is:

1. A method of applying therapeutic neural stimuli, the method comprising:
    monitoring for at least one of sensory input and movement of a user using a control unit; and
    in response to detection of at least one of sensory input and a user movement, delivering an increased stimulus dosage via at least one stimulus electrode within a period of time corresponding to a duration of time for which the detected sensory input or user movement gives rise to masking, the increased stimulus dosage being configured to give rise to increased neural recruitment.

2. The method of claim 1, wherein the increased stimulus dosage is effected by increasing one or more of the stimulus amplitude, the stimulus pulse width and/or the stimulus frequency.

3. The method of claim 2, wherein the increased stimulus dosage comprises a burst of high frequency stimuli.

4. The method of claim 1 wherein at times when neither sensory input nor movement is detected stimuli are delivered at a reduced dosage.

5. The method of claim 1 wherein at times when neither sensory input nor movement is detected no stimuli are delivered.

6. The method of claim 1 further comprising monitoring a cumulative stimulus dosage delivered to the user, and using the cumulative stimulus dosage as a basis to define a required stimulus regime either during or between movements in order to seek to deliver a desired total stimulus dosage.

7. The method of claim 1 wherein at least one of sensory input and movement of the user is detected by measuring neural activity upon the neural pathway.

8. The method of claim 7 wherein the measured neural activity comprises evoked neural responses resulting from electrical stimuli applied to the neural pathway.

9. The method of claim 8 wherein movement is detected when a change is detected in the neural response evoked from a given stimulus.

10. The method of claim 7 wherein the measured neural activity comprises non-evoked neural activity.

11. The method of claim 1 wherein movement of the user is detected by an accelerometer.

12. The method of claim 1 wherein the period of time within which the increased stimulus dosage is delivered is a predefined approximation of the duration of a typical human movement.

13. The method of claim 1 wherein the period of time for which the increased stimulus dosage is delivered is adaptively determined by performing the further step of detecting a cessation of sensory input or movement by the user, and in turn ceasing the delivery of the increased stimulus dosage.

14. The method of claim 1 wherein the increased stimulus dosage is delivered at select moments within the period of time.

15. A device for applying therapeutic neural stimuli, the device comprising:
    at least one electrode configured to be positioned alongside a neural pathway of a user; and
    a control unit configured to monitor for at least one of sensory input and movement of the user, and configured to deliver an increased stimulus dosage via the at least one electrode within a period of time corresponding to a duration of time for which the detected sensory input or user movement gives rise to masking, the increased stimulus dosage being configured to give rise to increased neural recruitment.

16. A method for effecting a neural blockade, the method comprising:
    delivering a sequence of electrical stimuli to neural tissue using at least one stimulus electrode, each stimulus configured at a level whereby at least at a given relative position of a stimulus electrode to the neural tissue a first stimulus of the sequence generates an action potential and whereby each subsequent stimulus alters a membrane potential of the neural tissue without causing depolarisation of the neural tissue nor evoking an action potential, each subsequent stimulus being delivered prior to recovery of the membrane potential of the neural tissue from a preceding stimulus such that the sequence of stimuli maintains the membrane potential in an altered range in which conduction of action potentials is hindered or prevented.

17. The method of claim 16, wherein the blockade is effected by applying a sequence of supra-threshold stimuli, the first of which will evoke an action potential.

18. The method of claim 16 wherein the blockade is effected by applying a sequence of stimuli which are sub-threshold in a first posture, but which become supra-threshold at times when the user moves to a second posture.

19. The method of claim 16 wherein the sequence of stimuli is delivered at a frequency greater than 500 Hz.

20. The method of claim 19 wherein the sequence of stimuli is delivered at a frequency greater than 1 kHz.

21. The method of claim 20 wherein the sequence of stimuli is delivered at a frequency in the range of 5-15 kHz.

22. The method of claim 16 wherein a nominal sub-threshold stimulation level is predetermined by a clinician at a time of fitting of an implanted stimulator for the user.

23. The method of claim 16 wherein the nominal sub-threshold level is adaptively determined by repeatedly determining a recruitment threshold of the neural tissue from time to time.

24. A device for effecting a neural blockade, the device comprising:
    at least one electrode configured to be positioned alongside a neural pathway of a user; and
    a control unit configured to deliver a sequence of electrical stimuli to neural tissue, each stimulus configured at a level whereby at least at a given relative position of the electrode to the neural tissue a first stimulus of the sequence generates an action potential and whereby each subsequent stimulus alters a membrane potential of the neural tissue without causing depolarisation of the neural tissue nor evoking an action potential, each subsequent stimulus being delivered prior to recovery of the membrane potential of the neural tissue from a preceding stimulus such that the sequence of stimuli maintains the membrane potential in an altered range in which conduction of action potentials is hindered or prevented.

25. A computer program product comprising computer program code means to make a computer execute a procedure, the computer program product comprising computer program code means for carrying out the method of claim 1.

26. A computer program product comprising computer program code means to make a computer execute a procedure, the computer program product comprising computer program code means for carrying out the method of claim 16.

* * * * *

UNITED STATES PATENT AND TRADEMARK OFFICE
CERTIFICATE OF CORRECTION

PATENT NO. : 10,632,307 B2
APPLICATION NO. : 15/327981
DATED : April 28, 2020
INVENTOR(S) : John Louis Parker Page 1 of 1

It is certified that error appears in the above-identified patent and that said Letters Patent is hereby corrected as shown below:

On the Title Page

Item (86) PCT No., "PCT/US2015/050422" should read -- PCT/AU2015/050422 --.

Signed and Sealed this
Eighteenth Day of August, 2020

Andrei Iancu
*Director of the United States Patent and Trademark Office*